(12) United States Patent
Reddy et al.

(10) Patent No.: US 10,980,570 B2
(45) Date of Patent: *Apr. 20, 2021

(54) IMPLANTATION OF AN ACTIVE MEDICAL DEVICE USING THE INTERNAL THORACIC VASCULATURE

(71) Applicant: CARDIAC PACEMAKERS, INC., St. Paul, MN (US)

(72) Inventors: G. Shantanu Reddy, Minneapolis, MN (US); Andrew L. De Kock, Ham Lake, MN (US); James O. Gilkerson, Stillwater, MN (US); James K. Cawthra, Jr., Ramsey, MN (US); Christopher Alan Fuhs, Roseville, MN (US); Daniel J. Foster, Lino Lakes, MN (US); Peter Hall, Andover, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 481 days.

This patent is subject to a terminal disclaimer.

(21) Appl. No.: 15/868,799

(22) Filed: Jan. 11, 2018

(65) Prior Publication Data
US 2018/0193060 A1    Jul. 12, 2018

Related U.S. Application Data

(60) Provisional application No. 62/445,403, filed on Jan. 12, 2017.

(51) Int. Cl.
*A61B 5/04* (2006.01)
*A61B 17/34* (2006.01)
(Continued)

(52) U.S. Cl.
CPC ............ *A61B 17/3468* (2013.01); *A61F 2/82* (2013.01); *A61N 1/05* (2013.01); *A61N 1/0504* (2013.01);
(Continued)

(58) Field of Classification Search
CPC ....... A61N 1/0504; A61N 1/056; A61N 1/057
See application file for complete search history.

(56) References Cited

U.S. PATENT DOCUMENTS 5,207,218 A * 5/1993 Carpentier ........... A61N 1/3752
                                                          607/36
5,331,966 A    7/1994 Bennett et al.
(Continued)

FOREIGN PATENT DOCUMENTS

WO    2016148928 A1    9/2016
WO    2016149262 A1    9/2016

OTHER PUBLICATIONS

Advisory Action Before the Filing of an Appeal Brief for U.S. Appl. No. 15/667,167, dated Mar. 21, 2019.
(Continued)

*Primary Examiner* — Alyssa M Alter
(74) *Attorney, Agent, or Firm* — Seager, Tufte & Wickhem LLP

(57) ABSTRACT

Implantation of a cardiac stimulus system using the intercostal veins. Superior, intercostal, and inferior access methods are discussed and disclosed. Superior access may be performed by entering the brachiocephalic vein from a jugular, subclavian, or other vein, and then accessing the internal thoracic vein, traversing a portion of the internal thoracic vein and then accessing an intercostal vein therefrom. Inferior access may be accomplished inferior to the lower rib margin via the superior epigastric vein, advancing superiorly into the internal thoracic vein and then accessing
(Continued)

an intercostal vein therefrom. Intercostal access may include creating an opening in an intercostal space between two ribs and advancing a needle using ultrasound guidance to enter the intercostal vein directly.

20 Claims, 30 Drawing Sheets

(51) Int. Cl.
*A61N 1/05* (2006.01)
*A61N 1/362* (2006.01)
*A61F 2/82* (2013.01)
*A61N 1/39* (2006.01)
*A61B 17/00* (2006.01)

(52) U.S. Cl.
CPC ............. *A61N 1/056* (2013.01); *A61N 1/057* (2013.01); *A61N 1/0563* (2013.01); *A61N 1/3621* (2013.01); *A61N 1/3627* (2013.01); *A61B 2017/00292* (2013.01); *A61F 2220/0016* (2013.01); *A61N 1/3956* (2013.01)

(56) References Cited

U.S. PATENT DOCUMENTS

| | | |
|---|---|---|
| 6,647,292 B1 | 11/2003 | Bardy et al. |
| 6,721,597 B1 | 4/2004 | Bardy et al. |
| 7,149,575 B2 | 12/2006 | Ostroff et al. |
| 7,655,014 B2 | 2/2010 | Ko et al. |
| 7,783,340 B2 | 8/2010 | Sanghera et al. |
| 7,818,068 B2 | 10/2010 | Meadows et al. |
| 7,962,222 B2 | 6/2011 | He et al. |
| 8,005,543 B2 | 8/2011 | Libbus et al. |
| 8,157,813 B2 | 4/2012 | Ko et al. |
| 8,386,048 B2 | 2/2013 | McClure et al. |
| 8,483,843 B2 | 7/2013 | Sanghera et al. |
| 8,543,216 B2 | 9/2013 | Carbunaru et al. |
| 8,718,793 B2 | 5/2014 | O'Connor |
| 2005/0043765 A1* | 2/2005 | Williams ............... A61N 1/057 607/9 |
| 2007/0213813 A1* | 9/2007 | Von Segesser ....... A61F 2/2433 623/2.18 |
| 2008/0071339 A1* | 3/2008 | Stalker ................. A61B 5/0215 607/119 |
| 2010/0191043 A1* | 7/2010 | Chin ................. A61B 17/00008 600/36 |
| 2012/0029335 A1 | 2/2012 | Sudam et al. |
| 2014/0114371 A1* | 4/2014 | Westlund ............. A61N 1/0558 607/20 |
| 2015/0025612 A1 | 2/2015 | Haasl et al. |
| 2015/0051610 A1 | 2/2015 | Schmidt et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0224320 A1 | 8/2015 | Stahmann |
| 2015/0297902 A1 | 10/2015 | Stahmann et al. |
| 2015/0352358 A1* | 12/2015 | Atwater ............. A61N 1/36578 607/17 |
| 2015/0360036 A1 | 12/2015 | Kane et al. |
| 2016/0038742 A1 | 2/2016 | Stahmann et al. |
| 2016/0059007 A1 | 3/2016 | Koop |
| 2016/0059022 A1 | 3/2016 | Stahmann et al. |
| 2016/0059024 A1 | 3/2016 | Stahmann et al. |
| 2016/0059025 A1 | 3/2016 | Stahmann et al. |
| 2016/0089539 A1 | 3/2016 | Gilkerson et al. |
| 2016/0228712 A1 | 8/2016 | Koop |
| 2016/0256692 A1 | 9/2016 | Baru |
| 2017/0021159 A1 | 1/2017 | Reddy et al. |
| 2017/0095657 A1 | 4/2017 | Reddy et al. |
| 2017/0112399 A1 | 4/2017 | Brisben et al. |
| 2017/0113040 A1 | 4/2017 | Brisben et al. |
| 2017/0113050 A1 | 4/2017 | Brisben et al. |
| 2017/0113053 A1 | 4/2017 | Brisben et al. |
| 2018/0036527 A1 | 2/2018 | Reddy et al. |
| 2018/0036547 A1 | 2/2018 | Reddy |
| 2018/0133462 A1 | 5/2018 | Reddy |
| 2018/0133463 A1 | 5/2018 | Reddy |
| 2018/0133494 A1 | 5/2018 | Reddy |
| 2018/0169384 A1 | 6/2018 | Reddy et al. |
| 2018/0169425 A1 | 6/2018 | Reddy et al. |
| 2018/0178018 A1 | 6/2018 | Reddy et al. |
| 2018/0178019 A1 | 6/2018 | Reddy et al. |
| 2018/0193060 A1 | 7/2018 | Reddy et al. |
| 2018/0214686 A1 | 8/2018 | De Kock et al. |
| 2018/0256890 A1 | 9/2018 | Fuhs et al. |
| 2018/0264270 A1 | 9/2018 | Koop et al. |
| 2018/0296824 A1 | 10/2018 | De Krock et al. |
| 2018/0325480 A1 | 11/2018 | Liu et al. |
| 2018/0344200 A1 | 11/2018 | Thakur et al. |
| 2018/0344252 A1 | 11/2018 | An et al. |

OTHER PUBLICATIONS

Final Office Action for U.S. Appl. No. 15/667,167, dated Jan. 10, 2019.
Non-Final Office Action for U.S. Appl. No. 15/667,167, dated Jun. 26, 2018.
Non-Final Office Action for U.S. Appl. No. 15/667,167, dated Aug. 7, 2019.
Final Office Action for U.S. Appl. No. 15/667,221, dated Apr. 11, 2019.
Non-Final Office Action for U.S. Appl. No. 15/667,221, dated Oct. 1, 2018.
Notice of Allowance and Fees Due for U.S. Appl. No. 15/667,221, dated Jul. 11, 2019.
Amendment for U.S. Appl. No. 15/667,167, dated Sep. 17, 2018.
Amendment for U.S. Appl. No. 15/667,167, dated Oct. 9, 2019.
Amendment After Final Office Action for U.S. Appl. No. 15/667,167, dated Mar. 11, 2019.
Request for Continued Examination (RCE) for U.S. Appl. No. 15/667,167, dated Apr. 10, 2019.
Amendment for U.S. Appl. No. 15/667,221, dated Dec. 21, 2018.
Amendment After Final Office Action for U.S. Appl. No. 15/667,221, dated May 22, 2019.
Moeinipour et al., "A Rare Central Venous Catheter Malposition: A Case Report," Anesth Pain Med., 4(1): 1-3, Feb. 5, 2014.
Schuder et al., "Experimental Ventricular Defibrillation with an Automatic and Completely Implanted System," Trans. Amer. Soc. Artif. Int. Organs, XVI: 207-212, 1970.
Schuder et al., "The Role of an Engineering Oriented Medical Research Group in Developing Improved Methods and Devices for Achieving Ventricular Defibrillation: The University of Missouri Experience," PACE, 16: 95-124, Jan. 1993.
Ghosh et al., "A Rare Malposition of the Thoracic Venous Catheter Introduced via the Left Internal Jugular Vein," Indian J. Crit. Care Med., 12(4): 201-203, Oct.-Dec. 2008.
Loukas et al., "The Clinical Anatomy of the Internal Thoracic Veins," Folia Morphol, 66(1): 25-32, 2007.

* cited by examiner

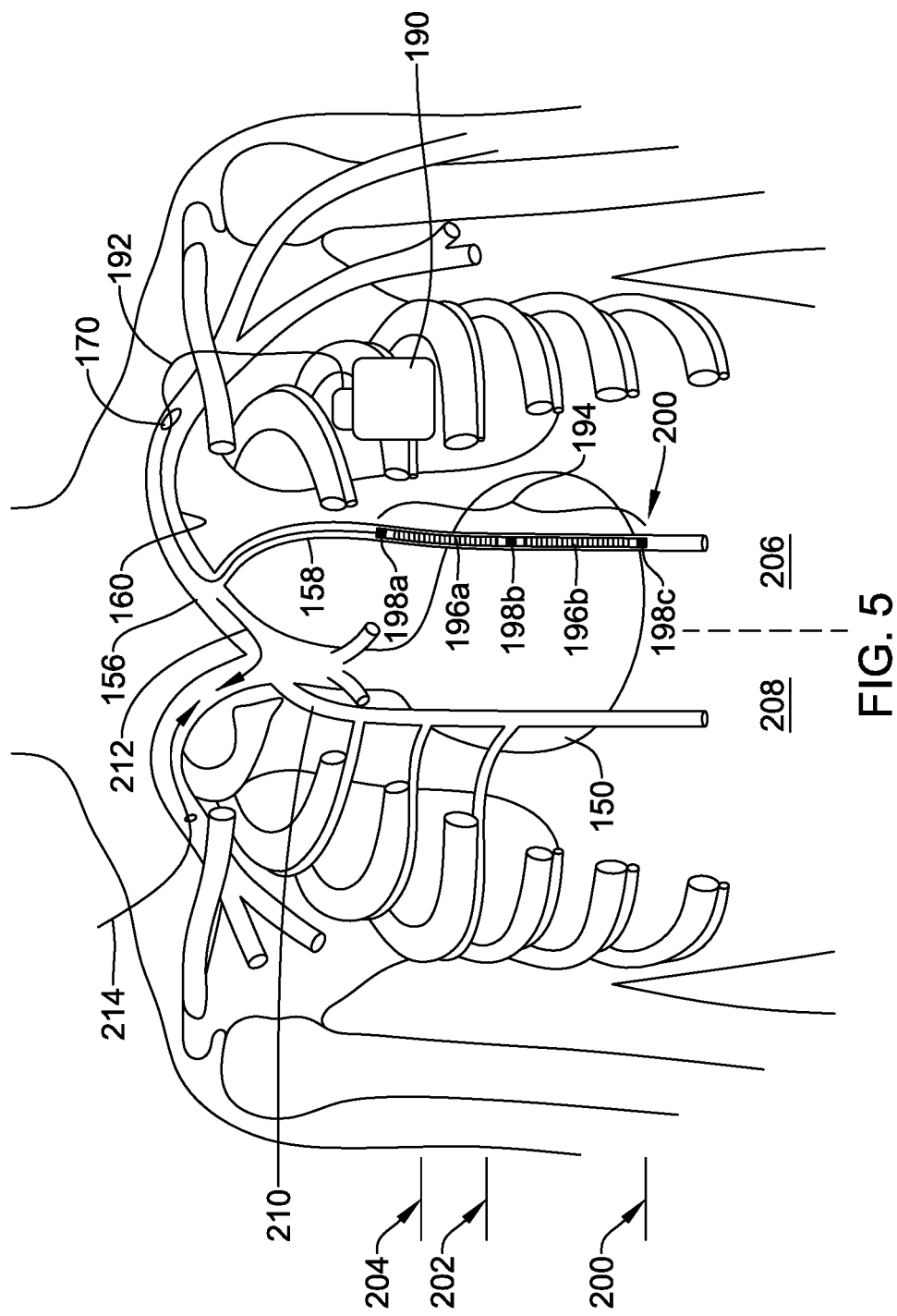

IMPLANTATION OF AN ACTIVE MEDICAL DEVICE USING THE INTERNAL THORACIC VASCULATURE

CROSS REFERENCE TO RELATED APPLICATIONS

The present application claims the benefit of and priority to U.S. Provisional Patent Application Ser. No. 62/445,403, filed Jan. 12, 2017 and titled IMPLANTATION OF AN ACTIVE MEDICAL DEVICE USING THE INTERNAL THORACIC VASCULATURE, the disclosure of which is incorporated herein by reference.

BACKGROUND

The implantable defibrillator has been demonstrated to extend patient lives by treatment of potentially deadly arrhythmias. Various efforts have been made to address complications associated with implantation of such devices. For example, early devices generally used epicardial patch electrodes implanted via thoracotomy, with attendant surgical risks and significant risks of failure of the epicardial patch electrodes and associated leads. The use of transvenous leads represented a major advance, avoiding thoracotomy and improving reliability. However, lead failure remained a significant issue, as the lead attachment in the heart cause the lead to flex with each heartbeat.

The advent of subcutaneous defibrillators allows avoidance of lead failure issues, with leads implanted beneath the skin and over the ribcage of the patient and not subjected to the repeated flexing. Subcutaneous defibrillators require higher energy for defibrillation, causing the pulse generators for such systems to be larger than their transvenous predecessors. Both bradycardia and anti-tachycardia pacing are of limited utility because subcutaneous pacing can be very uncomfortable for the patient. There remains interest in further alternative locations for implantable defibrillators and other medical devices such as the implantable pacemaker.

Overview

The present inventors have recognized, among other things that the internal thoracic vasculature including, in particular, the internal thoracic vein (ITV), sometimes also referred to as the internal mammary vein, presents an opportunity for an additional alternative implant location or access to alternative implant locations. A lead for an implantable cardiac device may be implanted into one or both ITVs. Alternatively or additionally, a lead may be implanted in an intercostal vein.

In a first example, a method of implanting a lead for use in a cardiac stimulus system in a patient, the lead having at least one electrode thereon may comprise inserting the lead into an intercostal vein to a desired location relative to the heart of a patient.

Alternatively or additionally to any of the examples above, in another example, the method may further comprise establishing access to a brachiocephalic vein of the patient and advancing a distal portion of the lead through the ostium of an internal thoracic vein (ITV) from the brachiocephalic vein, and then advancing a distal portion of the lead through the ITV and into the intercostal vein.

Alternatively or additionally to any of the examples above, in another example, the step of establishing access to the brachiocephalic vein may comprise inserting an introducer sheath into one of the axillary, jugular, cephalic or subclavian veins of the patient and advancing at least the lead through the introducer sheath, into the brachiocephalic vein, and then through the ostium of the ITV.

Alternatively or additionally to any of the examples above, in another example, the method may further comprise advancing a guidewire to and into the ostium of the ITV.

Alternatively or additionally to any of the examples above, in another example, the method may further comprise advancing a guide catheter to and into the ostium of the ITV.

Alternatively or additionally to any of the examples above, in another example, the method may further comprise advancing the guide catheter to and into the intercostal vein.

Alternatively or additionally to any of the examples above, in another example, the method may further comprise establishing access to the intercostal vein through an intercostal space between two ribs including inserting a needle into one of the intercostal veins through the intercostal space and advancing a sheath into the intercostal space and into the intercostal vein. The step of inserting the lead may comprise advancing the distal end of the lead through the sheath and into the intercostal vein.

Alternatively or additionally to any of the examples above, in another example, the step of advancing the distal end of the lead through the sheath and into the intercostal vein may comprise advancing the distal end of the lead in a posterior direction.

Alternatively or additionally to any of the examples above, in another example, the method may further comprise advancing the distal end of the lead into the azygos vein system.

Alternatively or additionally to any of the examples above, in another example, the method may further comprise tunneling from the left axilla to the intercostal space, attaching an implantable pulse generator to the lead and implanting the pulse generator at the left axilla.

Alternatively or additionally to any of the examples above, in another example, the method may further comprise establishing access to the superior epigastric vein at a location inferior to the lower rib margin and introducing the lead through the epigastric vein and superiorly into the ITV, and then advancing a distal portion of the lead through the ITV and into the intercostal vein.

Alternatively or additionally to any of the examples above, in another example, the method may further comprise establishing access to the musculophrenic vein at about the lower rib margin and introducing the lead through the epigastric vein and superiorly into the ITV, and then advancing a distal portion of the lead through the ITV and into the intercostal vein.

Alternatively or additionally to any of the examples above, in another example, the step of establishing access to the superior epigastric vein may comprise inserting a needle into the superior epigastric vein and advancing a sheath into the superior epigastric vein. The step of introducing the lead through the superior epigastric vein may comprise advancing the distal end of the lead through the sheath and into the ITV.

Alternatively or additionally to any of the examples above, in another example, the method may further comprise tunneling from the left axilla to the location where the ITV is accessed and a proximal portion of the lead is in the tunnel. The method may further comprise attaching an implantable pulse generator to the lead and implanting the pulse generator at the left axilla.

Alternatively or additionally to any of the examples above, in another example, the method may further comprise anchoring the lead in the intercostal vein using an inflatable balloon.

Alternatively or additionally to any of the examples above, in another example, the method may further comprise anchoring the lead in the intercostal vein using an expandable member, the expandable member selected from the group consisting of a lobe, a tine, a hook, or a stent.

Alternatively or additionally to any of the examples above, in another example, the lead may be configured to have a curvature and the method may further comprise anchoring the lead by allowing it to assume the curvature once inserted into the intercostal vein.

Alternatively or additionally to any of the examples above, in another example, the method may further comprise attaching a suture sleeve and suturing the suture sleeve subcutaneous tissue to the lead to hold the lead in position.

Alternatively or additionally to any of the examples above, in another example, the intercostal vein may be a right intercostal vein.

Alternatively or additionally to any of the examples above, in another example, the intercostal vein may be a left intercostal vein.

Alternatively or additionally to any of the examples above, in another example, the method may further comprise advancing a second lead into the ITV.

In another example, a method of implanting a cardiac stimulus system may comprise performing the method of any of the above examples to implant a first lead in a left intercostal vein, implanting a second lead in the left ITV, and coupling the first and second leads to a pulse generator for the cardiac stimulus system.

In another example, a method of treating a patient may comprise delivering therapy between a first electrode disposed on a lead which is placed in an intercostal vein and at least a second electrode.

Alternatively or additionally to any of the examples above, in another example, the therapy may be a defibrillation therapy.

Alternatively or additionally to any of the examples above, in another example, the therapy may be a bradycardia pacing therapy.

Alternatively or additionally to any of the examples above, in another example, the therapy may be an anti-tachycardia pacing therapy.

Alternatively or additionally to any of the examples above, in another example, the therapy may be a cardiac resynchronization therapy.

Alternatively or additionally to any of the examples above, in another example, the first electrode may be in a right intercostal vein and the second electrode may be in a right internal thoracic vein (ITV).

Alternatively or additionally to any of the examples above, in another example, the first electrode may be in a left intercostal vein and the second electrode may be in a left internal thoracic vein (ITV).

Alternatively or additionally to any of the examples above, in another example, the first and second electrodes may be coupled to an internal pulse generator also implanted in the patient.

Alternatively or additionally to any of the examples above, in another example, the implantable pulse generator may be in the left axilla.

Alternatively or additionally to any of the examples above, in another example, the implantable pulse generator may be placed in a subclavicular pectoral position on the patient's chest.

Alternatively or additionally to any of the examples above, in another example, the therapy may be a defibrillation therapy and the second electrode may be disposed subcutaneously on a lead in the patient.

Alternatively or additionally to any of the examples above, in another example, the therapy may be a defibrillation therapy, wherein the first electrode may be electrically in common with a third electrode during the therapy delivery.

Alternatively or additionally to any of the examples above, in another example, the first electrode may be a composite electrode including at least a first coil electrode electrically and one or more ring electrodes.

Alternatively or additionally to any of the examples above, in another example, the first electrode may be a composite electrode including at least first and second coil electrodes.

Alternatively or additionally to any of the examples above, in another example, the second electrode may be a coil electrode.

Alternatively or additionally to any of the examples above, in another example, the second electrode may be a multi-electrode structure.

In another example, an implantable cardiac stimulus device may comprise a lead and an implantable canister for coupling to the lead. The implantable canister may house operational circuitry configured to deliver output therapy in the form of at least one of bradycardia pacing, anti-tachycardia pacing, cardiac resynchronization therapy, or defibrillation, according to any of the examples above.

In another example, a method of implanting a lead for use in a cardiac stimulus system in a patient, the lead having at least one electrode thereon may comprise inserting a distal end of a lead into an intercostal vein, advancing the lead to a desired location relative to the heart of a patient, and securing the lead in place.

Alternatively or additionally to any of the examples above, in another example, an implantation tool set may be configured for use in any of the examples above.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 4-5 show superior access to and implantation of a lead in the left ITV;

DETAILED DESCRIPTION

Figure 1A:
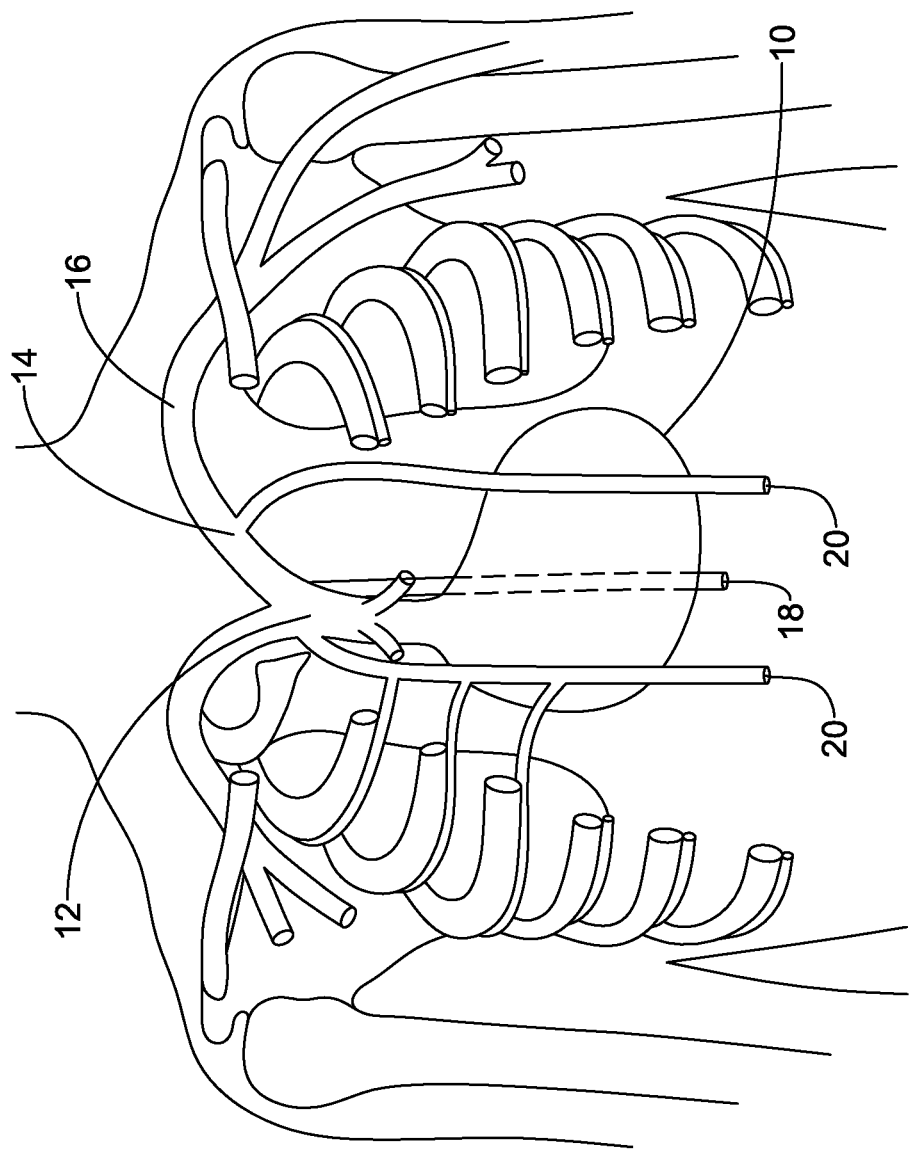
FIGS. 1A-1B illustrate the thoracic anatomy including placement of the internal thoracic veins (ITVs)

The S-ICD System from Boston Scientific provides benefits to the patient including the preservation of transvenous anatomy and avoidance of intracardiac leads, which may fracture and/or may serve as conduits for infection to reach the heart, and can occlude blood vessels going into the heart, making later placement of leads or other devices in the heart more difficult. Some examples and discussion of subcutaneous lead implantation may be found in U.S. Pat. No. 8,157,813, titled APPARATUS AND METHOD FOR SUBCUTANEOUS ELECTRODE INSERTION, and US PG Publication No. 20120029335, titled SUBCUTANEOUS LEADS AND METHODS OF IMPLANT AND EXPLANT, the disclosures of which are incorporated herein by reference. Additional subcutaneous placements are discussed in U.S. Pat. No. 6,721,597, titled SUBCUTANEOUS ONLY IMPLANTABLE CARDIOVERTER DEFIBRILLATOR AND OPTIONAL PACER, and the above mentioned U.S. Pat. No. 7,149,575, the disclosures of which are incorporated herein by reference.

While many patients can be well treated with the S-ICD System, there continue to be limitations. Increased energy requirements of the S-ICD System, perceived difficulty with providing chronic bradycardia pacing, and unavailability of anti-tachycardia pacing terminate select fast tachycardias, have created interest in alternative defibrillator and/or pacemaker placement techniques. One proposal has included a substernal placement, with a lead extending beneath the sternum from a position inferior to the lower rib margin, such as in US PG Patent Application Pub. No. 20170021159, titled SUBSTERNAL PLACEMENT OF A PACING OR DEFIBRILLATING ELECTRODE, the disclosure of which is incorporated herein by reference. Proposals for a substernal device have been referred to as extravascular, insofar as the lead does not enter or reside in the vasculature. Such devices are distinct from early generation epicardial devices in that the lead and electrode would not touch the heart or enter or be secured to the pericardium.

The present inventors have identified still a further alternative. In human anatomy, the internal thoracic vein (ITV), which may also be referred to as the internal mammary vein, is a vessel that drains the chest wall and breasts. There are both left and right internal thoracic veins on either side of the sternum, beneath the ribs. The ITV arises from the superior epigastric vein, accompanies the internal thoracic artery along its course and terminates in the brachiocephalic vein. The inventors have recognized that the ITV may make a suitable location for placement of a cardiac stimulus lead. In some instances, another lead may be placed in an intercostal vein, as described in more detail herein. The intercostal veins are veins that drain the rib cage's intercostal spaces. Anterior intercostal veins drain the anterior intercostal space into the internal thoracic veins while posterior intercostal veins drain into the azygos system of veins. While much of the following disclosure focuses on the use of the ITV, the intercostal veins, and/or veins connected to the ITV and/or intercostal veins many of these concepts could also be applied to the internal thoracic arteries, intercostal arteries and/or arteries connected to the internal thoracic arteries or intercostal arteries, which may sometimes be referenced as the internal mammary arteries.

FIG. 1A illustrates the thoracic anatomy including location of the internal thoracic veins (ITVs). An outline of the heart is shown at 10, with the superior vena cava (SVC) shown at 12. The brachiocephalic veins 14 couple to the SVC and extend past various cephalic branches to the subclavian vein 16. The azygos vein is shown at 18, and the right and left ITV are shown 20.

Figure 1B:
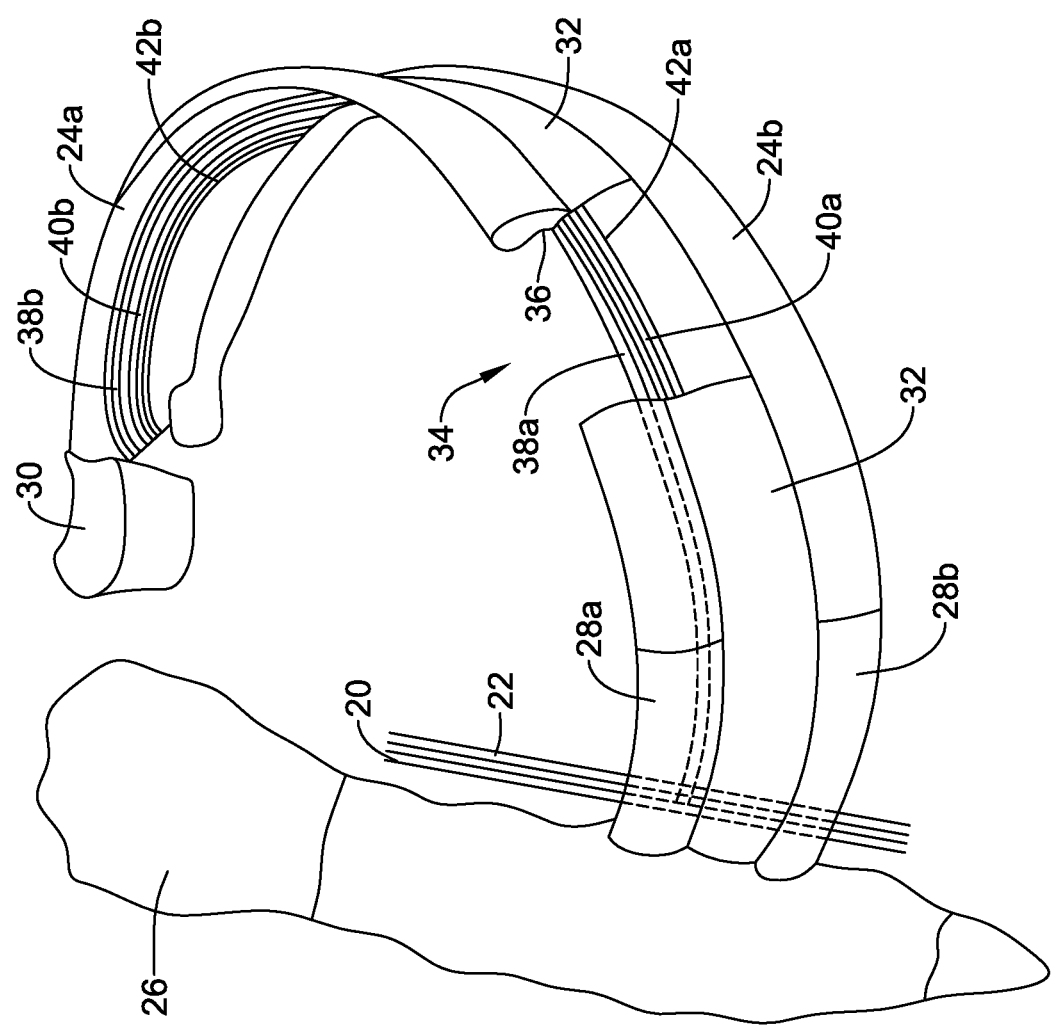

FIG. 1B illustrates an alternative view of some of the left thoracic anatomy. The ribs 24a, 24b (collectively, 24) are connected anteriorly to the sternum 26 through costal cartilage 28a, 28b (collectively, 28) and are coupled posteriorly to the spine 30. It should be understood that for clarity, not all of the ribs 24, or other anatomy that may be present, are illustrated. Intercostal muscle 32 extends between the ribs 24. A region of one of the ribs 24a, and a portion of the intercostal muscle 32 has been removed at the area generally indicated by arrow 34 to expose the anterior intercostal vein 38a, the anterior intercostal artery 40a, and the anterior intercostal nerve 42a disposed in or adjacent to the costal groove 36. Each rib in the ribcage includes an intercostal vein, artery, and nerve.

The anterior intercostal vein 38a follows the rib 24a laterally and posteriorly to become the posterior intercostal vein 38b. Similarly, the anterior intercostal artery 40a and the anterior intercostal nerve 42a follow the rib 24a laterally and posteriorly to become the posterior intercostal artery 40b and the posterior intercostal nerve, respectively. The left anterior intercostal veins 38a drain to the left ITV 20, shown next to the internal thoracic artery 22. The anterior intercostal vein 38a is shown in phantom under the rib 24a to further illustrate this connection between the ITV 20 and the anterior intercostal vein 38a. While not explicitly shown, the right anterior intercostal veins drain to the right ITV. The posterior intercostal veins 38b drain to the azygos vein system. The superior left posterior intercostal veins drain to the accessory hemiazygos vein, the inferior left posterior intercostal veins drain to the hemiazygos vein and the right posterior intercostal veins drain to the azygos vein.

Figure 2:
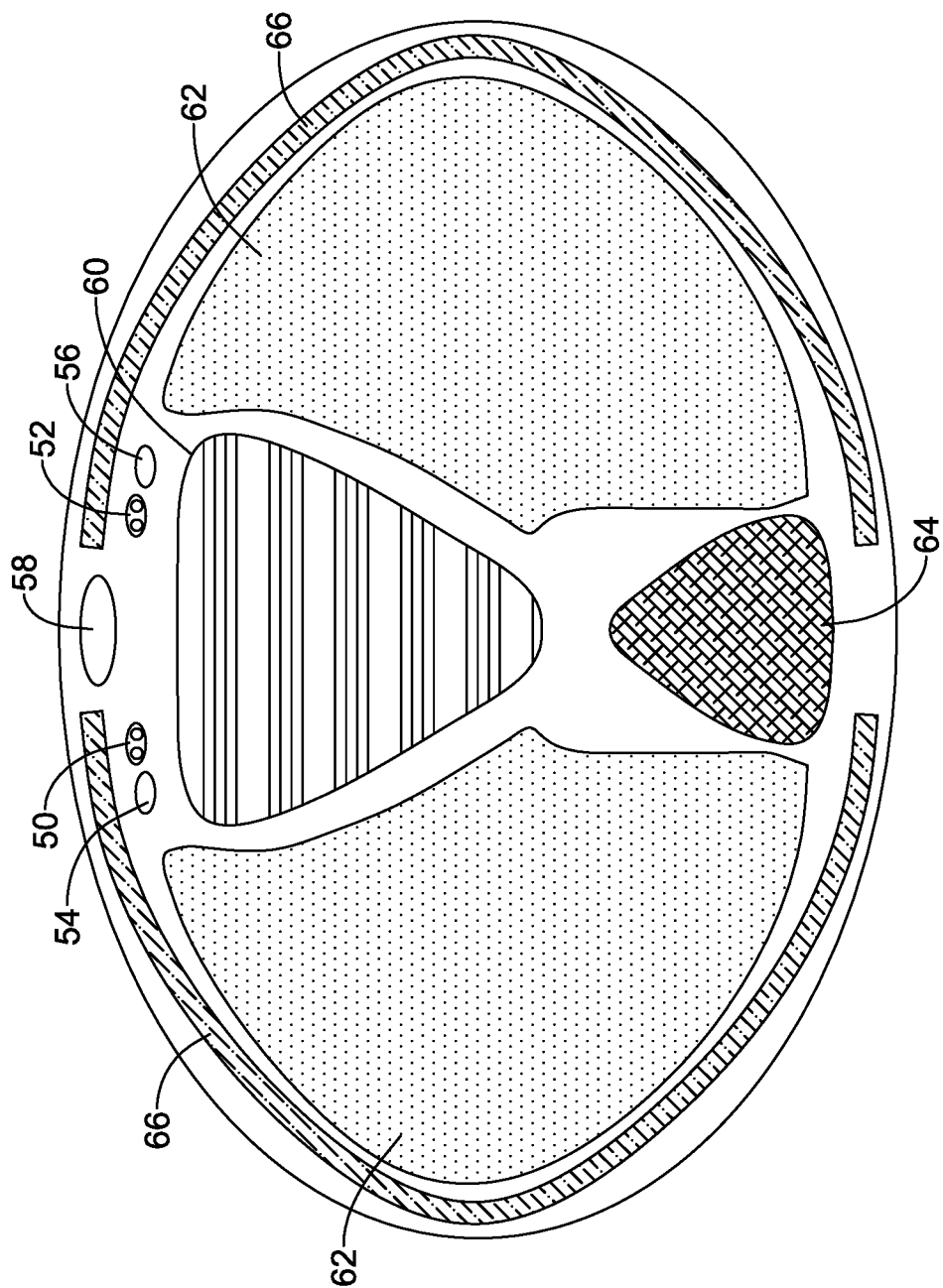
FIG. 2 shows the torso in a section view to highlight the location of the ITVs and arteries.

FIG. 2 shows the torso in a section view to highlight the location of the ITVs and internal thoracic arteries. More particularly, in the example, the left and right ITV are shown at 50, 52, running parallel to and more central of the internal thoracic arteries 54, 56, on either side of the sternum 58. The heart is shown at 60, with the lungs at 62 and spinal column at 64. The ITV 50, 52 lie beneath the ribs 66 but outside and separate from the pleurae of lungs 62. As used herein, the "ITV" is the name applied for the vein while it runs beneath the chest, that is, superior to the lower margin of the ribs. Inferior to the lower margin of the ribs, the blood vessel continues as the superior epigastric vein. The relatively superficial position makes the ITV 50, 52 accessible percutaneously inferior to the rib margin or through intercostal spaces between ribs 66 as further discussed below. Access to the ITV from an access point inferior to the lower rib margin may be described as accessing the ITV via the superior epigastric vein. Also shown in some examples below are methods to access to the ITV via the superior vasculature, including the brachiocephalic vein.

Figure 3B:
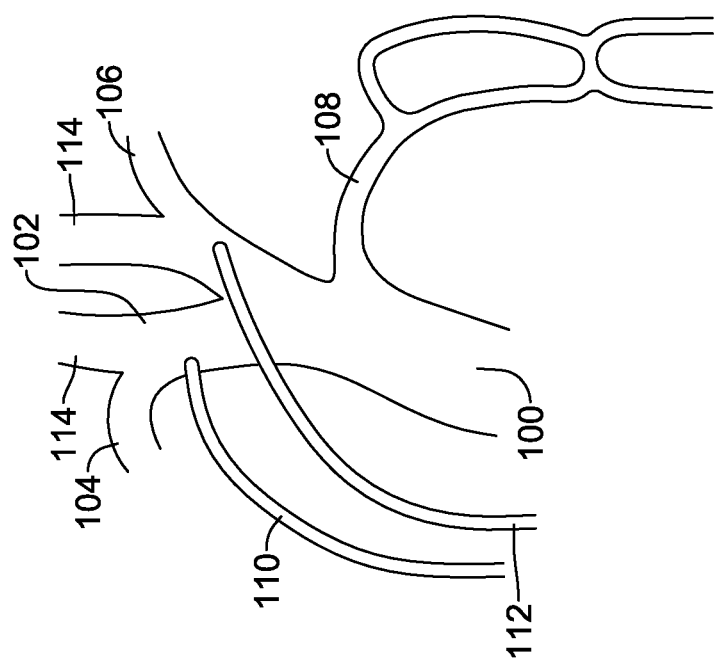
FIGS. 3A-3B show the ITVs and linked vasculature in isolation.
Figure 3A:
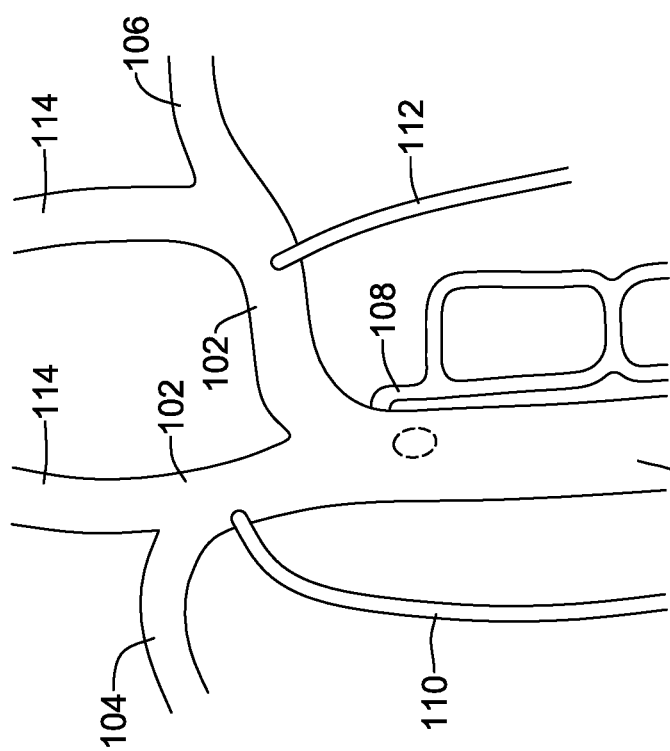

FIGS. 3A-3B show the ITV and linked vasculature in isolation. FIG. 3A is an anterior view of selected portions of the venous structure of the upper torso, and FIG. 3B is a lateral view of the same. The SVC is shown at 100, with the brachiocephalic veins 102 splitting at the upper end of the SVC. The right subclavian vein is at 104, and the left subclavian vein is at 106. The azygos vein is included in the illustration at 108, extending off the posterior of the SVC, and runs inferiorly posterior of the heart as can be understood from the lateral view of FIG. 3B. The right and left ITV are shown at 110, 112. These each branch off at a location that is considered part of the brachiocephalic veins 102. The internal jugular veins are also shown at 114.

Figure 4:
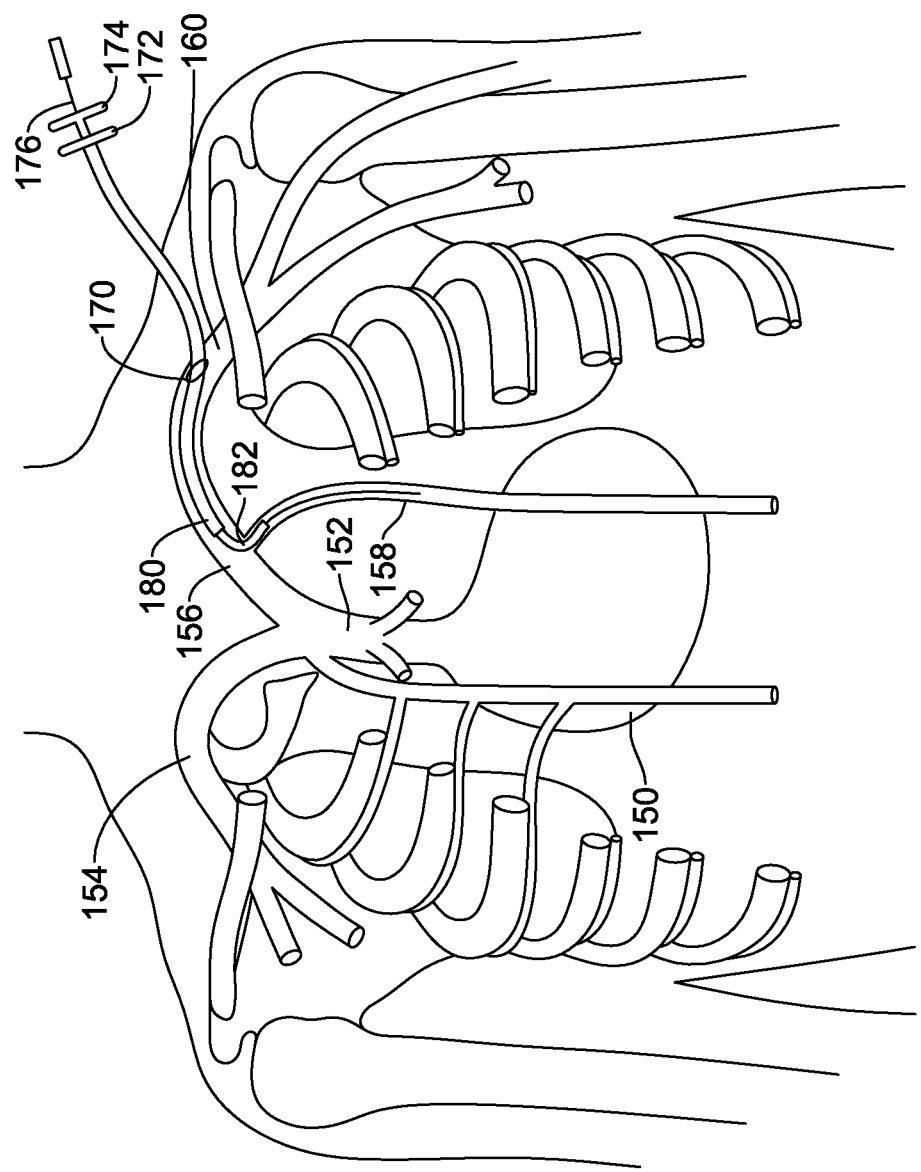

FIGS. 4-5 show superior access to and implantation of a lead in the ITV. Starting with FIG. 4, the heart is shown at 150 with the SVC at 152 and the brachiocephalic vein right branch at 154 and left branch at 156. Access to the subclavian vein 160 is shown at 170 using standard access techniques known in the art for implanting traditional transvenous pacemakers and defibrillators. For example, the Seldinger technique may be used by creating a puncture with a hollow needle or trocar, for example under ultrasound guidance, introducing a guidewire through the needle, removing the needle, and then inserting an introducer sheath 172, which may have a valve at its proximal end, over the guidewire. Other venipuncture or cutdown techniques may be used instead. Other vessels may be accessed instead of the subclavian vein using similar techniques including, for example, the jugular, cephalic, or axillary veins.

Into the access at 170, an introducer sheath 172 is inserted and advanced to a location to place its distal tip 180 near the ostium of the left ITV 158. Contrast injection may be useful to visualize the ITV structures and the ostia of the ITVs. A guide catheter 174 and guidewire 176 are then introduced through the introducer sheath 172. In other examples, a shorter introducer sheath may be used, with the guide catheter 174 used to traverse the distance to the relevant ostium.

The guidewire may be the same as used in gaining initial access 170 (if one is used to gain access 170), or may be a different guidewire. In an example, the guidewire 176 is preloaded in the guide catheter and both are introduced at the same time until the guide catheter 174 is at a desired location relative to the ostium of the selected ITV. The guidewire 176, which may be deflectable or steerable, can then be used to enter the left ITV 158 through the ostium thereof, passing down into the left ITV 158. The guide catheter 174 can then traverse over the guidewire and through the ostium and into the left ITV 158.

A device passing into the ITV from a superior position will need to pass through the valves of the ITV in a direction counter to their natural tendency (the veins prevent blood from flowing inferiorly). For an example where the guidewire passes unsupported by a guide catheter into the ITV from a superior position, the guidewire may preferably be stiff. In some examples, at least two guidewires may be used, a first more flexible and steerable guidewire to obtain initial access via the ostium of the ITV, and a second, stiffer guidewire that is sufficiently pushable to allow passage through the valves in the ITV.

In some examples, the guide catheter 174 is introduced first and the guidewire 176 is introduced next. For example, a steerable or curved guide catheter 174 may traverse the introducer sheath 172 to its distal end 180 and then, using steering of the guide catheter or a precurved structure of the guide catheter, would then turn as shown at 182 to enter the left ITV 158. The guidewire 176 may be introduced through the guide catheter 174. In another example, a guidewire 176 may be omitted.

FIG. 5 shows implantation of an implantable cardiac stimulus system. The system includes an implantable pulse generator 190 which may be placed in the subclavicular location shown (or any other suitable position, as desired). A lead 192 passes into the venous access point 170 into the subclavian vein 160 and to the brachiocephalic vein 156. The lead then enters the left ITV 158. For such an introduction, in one example, the guide catheter 174 (FIG. 4) can be used to direct the lead 192 through the ostium of the chosen ITV, with or without use of a guidewire 176 (FIG. 4).

In some examples, a flexible lead is used having a lumen therein to receive a guidewire or stylet to enhance pushability through the valves of the ITV 158. In another example, a flexible lead may be introduced with the support of the guide catheter 174 during advancement. In this latter example, the guide catheter 174 may receive the lead 192 through a guide catheter lumen that serves to retain a fixation apparatus or shape for the flexible lead, such as a 2-dimensional or 3-dimensional curvature (see FIGS. 10-11), tines (see FIG. 12), an expandable member (see FIG. 15), or hooks or a side-extending engagement structure (see FIG. 16).

In another alternative, the guide catheter 174 and guidewire 176 may be omitted by providing a lead with a flexible or steerable structure, and/or a lead configured for implantation using a steerable stylet. For example, a lead may be configured to be implanted using a steerable stylet in a lumen thereof, with the initial placement into the ostium of the left ITV 158 (or right ITV 210, if desired) at the distal end of the introducer sheath 172, possibly using contrast visualization, if desired. Once initial access is achieved, simply pushing the stylet should be sufficient to implant the lead to a desired level in the ITV. The stylet may have a secondary function of preventing an anchoring structure of the lead from assuming an anchoring shape or releasing an anchoring tine, hook, expandable member, stent or other device.

In the example, the lead 192 includes a multi-electrode distal structure as shown at 194. The structure includes a proximal coil 196A separate from a distal coil 196B. The coils 196A/B and canister 190 may serve as therapy delivery electrodes. As such there may be multiple therapy vectors such as between coil 196A and coil 196B, between either of coils 196A and 196B and the canister 190, or between a combination of two of the three therapy electrodes 196A, 196B and canister 190, and the third such electrode, such as by linking coils 196A and 196B in common as the anode or cathode relative to the canister 190.

A plurality of ring electrodes may be provided as shown at 198A, 198B, and 198C. Electrode 198C may also or instead be a tip electrode. Electrodes 198A/B/C may serve as sensing electrodes. The coils 196A, 196B may also serve as sensing electrodes. These various electrodes may be used for sensing cardiac signals in various combinations using, for example, methods and circuitry discussed in U.S. Pat. No. 7,783,340, titled SYSTEMS AND METHODS FOR SENSING VECTOR SELECTION IN AN IMPLANTABLE MEDICAL DEVICE USING A POLYNOMIAL APPROACH, and U.S. Pat. No. 8,483,843, SENSING VECTOR SELECTION IN A CARDIAC STIMULUS DEVICE WITH POSTURAL ASSESSMENT, and/or US PG Patent Application Pub. Nos. 20170112399, 20170113040, 20170113050, and 20170113053, the disclosures of which are incorporated herein by reference.

In addition, one or more of the ring or tip electrodes 198A, 198B, 198C may be used for therapy delivery. In an example, defibrillation therapy may use coils 196A, 196B coupled in common as the opposing pole to the canister 190, while pacing therapy may use coils 196A and 198B as opposing electrodes for post-shock pacing therapy, with a still different combination of electrodes used to provide ventricular pacing therapy for example by pacing between coil 196B and tip electrode 198C.

Line 202 is provided, illustratively, to separate the atria and ventricles. The lead 192 may be placed as shown such that the proximal coil 196A is about level with the atria, and distal coil 196B is about level with the ventricles, if desired. In some examples fewer or different electrodes may be provided on the lead 192 such as by excluding one or the other of the proximal coil 196A or distal coil 196B. Various designs are also shown herein.

Line 204 is provided to indicate the top of the heart, with the apex or bottom of the heart marked at 200. In some examples, one or more electrodes on the lead 192 are provided at or inferior to the apex 200, or at or superior to the top 204 of the heart. In the example shown, on the other hand, the electrodes are located generally between the apex 200 and top 204 of the heart.

The illustration shown in FIG. 5 places the lead on the left side 206 of the patient. In other examples, the right side 208 of the patient may instead or in addition be accessed, including the right ITV 210. Access to the right ITV 210 may be achieved by advancing a guide catheter and/or guidewire from the left subclavian access 170 as shown by arrow 212 across to the ostium of the right ITV 210.

Alternatively, access to the right ITV may be achieved as shown at arrow 214 by entering the right subclavian vein in a mirror image procedure of that shown in FIG. 4. In some examples, each of the left and right ITV 158, 210 may receive a lead 192. The lead 192 may be split (as shown relative to an inferior access route in FIG. 8B), a yoke may be provided near the canister 190 to join two leads together, or a header on the canister 190 may be configured to receive more than one lead 192, if desired, to provide leads in each of the left and right ITV 158, 210. If two leads are provided, use may be similar to that explained relative to FIG. 8A, except insofar as the leads may be implanted from the superior blood vessels as shown in FIG. 5. For example, pacing between right and left side lead placements may be performed to target specific chambers or chamber combinations, or sensing may be performed using one pair of electrodes with therapy delivery using a different pair of electrodes to achieve resynchronization or other desirable effect.

Figure 6A:
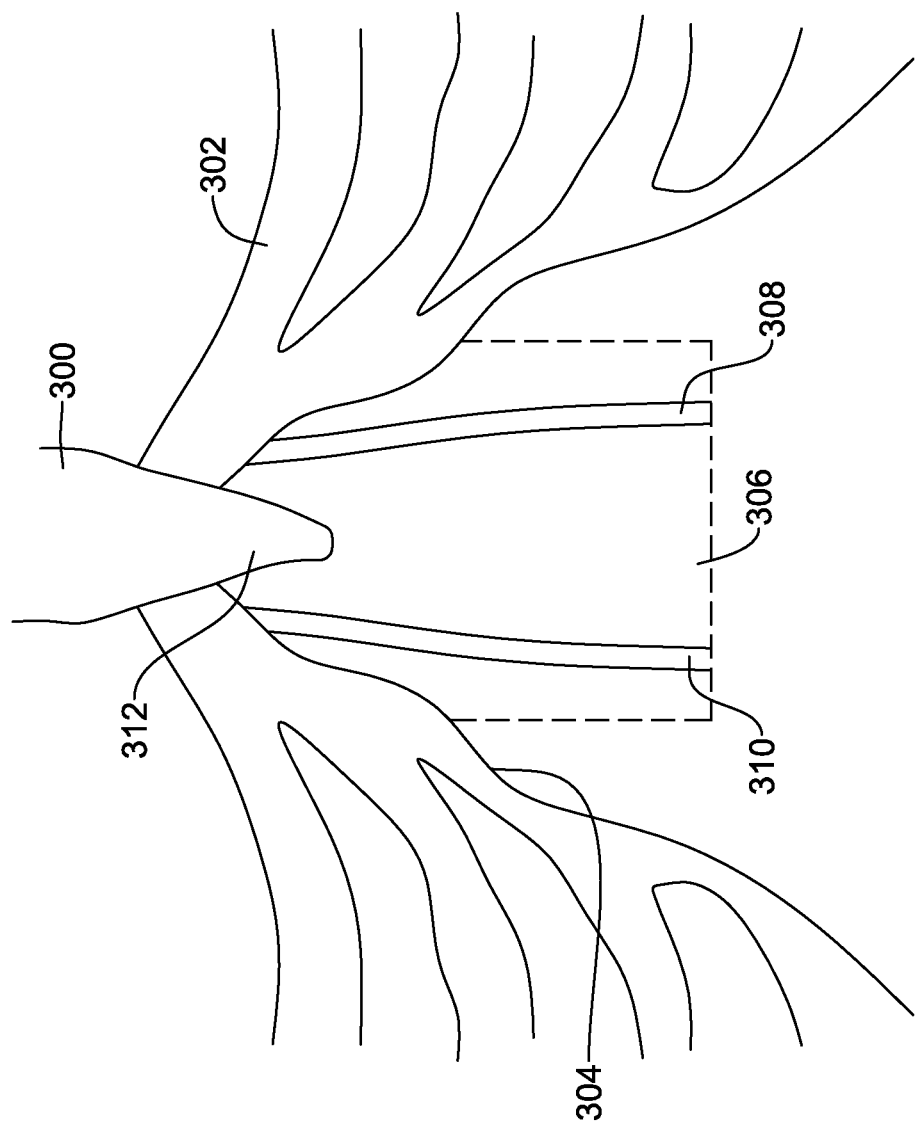
FIG. 6A shows in close view a location inferior to the lower rib margin where the ITV may be accessed inferiorly via the superior epigastric vein.

FIG. 6A shows in close view a location inferior to the lower rib margin where the ITV may be accessed inferiorly. This region may be referred to as the inferior thoracic aperture. The patient anatomy is shown in part including the sternum 300 and ribs 302, with the lower rib margin at 304.

A cutout area is shown at 306 in order to illustrate the approximate location for accessing the right or left ITV using the superior epigastric veins. The left superior epigastric vein is shown at 308, and the right superior epigastric vein is shown at 310. In order to access either vein 308, 310, a physician may palpate for the xiphoid process 312 and then use ultrasound guided access to obtain needle entry into the desired vein 308, 310 on the desired side of the xiphoid 312. This inferior approach preserves the upper thoracic vasculature in the event that the patient later needs a traditional transvenous, intracardiac system, or for use in other procedures. Such access may also reduce the potential for lead fracture such as that caused by subclavian crush. Once access to a selected superior epigastric vein 308, 310 is achieved, the vessel can be traversed in a superior direction to place the lead at a desired level by entering the corresponding ITV.

The access may generally resemble the well-known Seldinger technique, with an initial needle puncture using a hollow needle or trocar. A guidewire is passed through the hollow needle or trocar, which can then be removed. An introducer sheath, typically having a dilator therein and a valve at a proximal end thereof, is then inserted over the guidewire and into the desired blood vessel. The dilator and/or guidewire can then be removed, leaving in place the valved introducer sheath to allow introduction of interventional devices and/or a lead therethrough. At the conclusion of the lead implantation procedure, a sealing device such as a suture sleeve can be placed to seal the puncture site to the implantable lead left therein. The aim may be to access the ITV or superior epigastric vein at or near the $7^{th}$ rib margin in a window adjacent to the xiphoid process that may be described as a paraxiphoid window. In another example, a cut-down technique may be used to access the desired vein 308, 310 by incision through the skin. Next, possibly after visual confirmation the desired vessel is accessed, incision into the selected vein can be made. In another example, anatomical landmarks such as the rib margin and/or infrasternal angle may be used to facilitate venipuncture into the desired vein 308, 310.

The musculophrenic vein (not shown) runs along the lower rib margin 304 and may instead, or also, be accessed in a manner that will be termed, for purposes herein, as an inferior access location as it would be inferior to the lowest rib. The musculophrenic vein and superior epigastric vein come together at the lowest end of the ITV. The musculophrenic vein may be accessed using similar methods as for the superior epigastric vein such as by ultrasound-guided Seldinger technique. Due to its adjacency to a bony structure (the costal margin at 304), the musculophrenic vein may be useful as its access may be simpler than that of the superior epigastric vein, as the position can be readily ascertained. Further details on use of the musculophrenic vein for ITV access can be found in U.S. patent application Ser. No. 15/667,167, titled IMPLANTATION OF AN ACTIVE MEDICAL DEVICE USING THE INTERNAL THORACIC VASCULATURE, the disclosure of which is incorporated herein by reference.

Figure 6B:
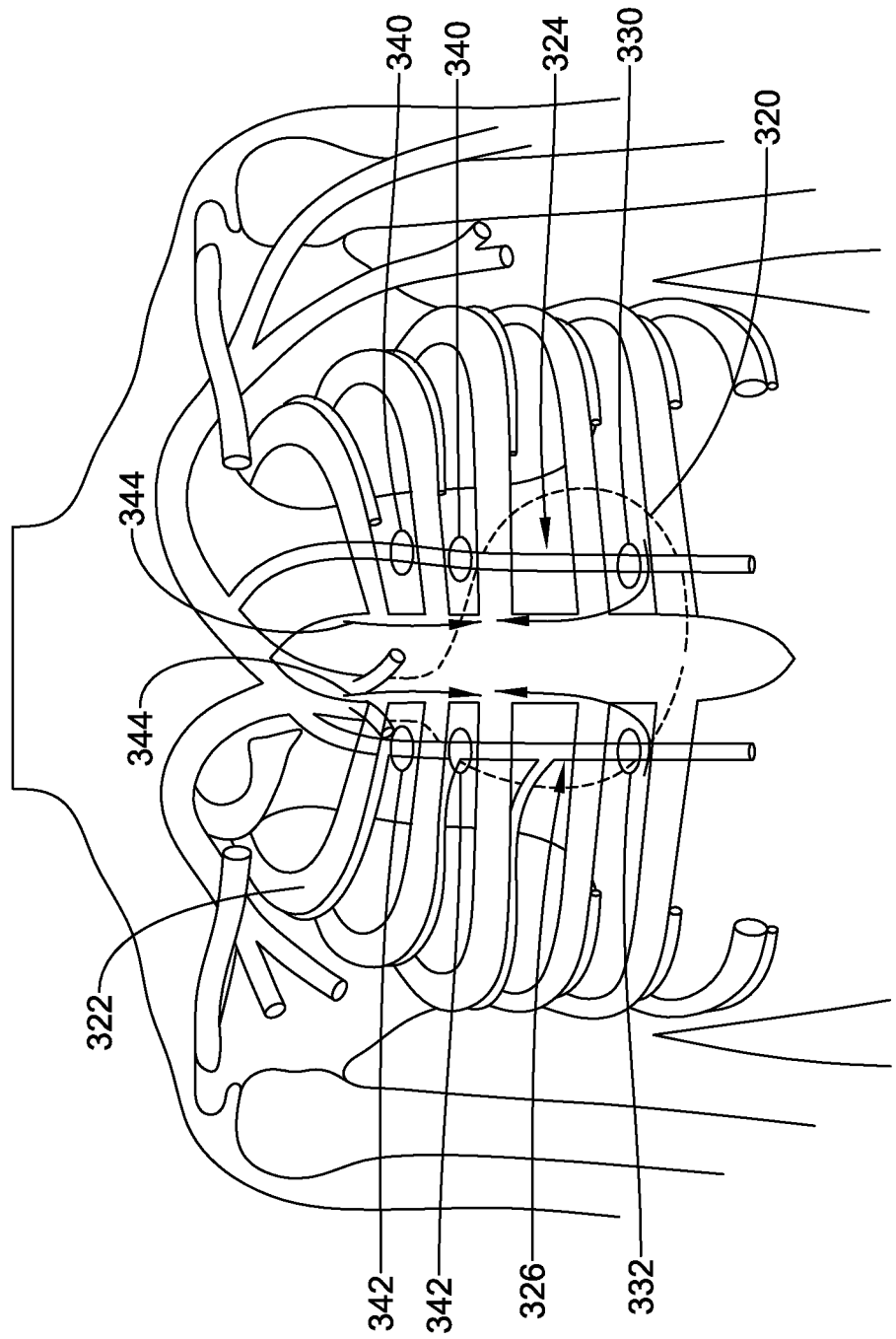
FIG. 6B illustrates intercostal access locations usable for superior or inferior access.

FIG. 6B illustrates some intercostal access locations usable for superior or inferior access. The Figure shows the heart at 320 beneath the ribcage 322. The right and left ITV are shown at 324 and 326. Any intercostal space overlying either of the right and left ITV may be a suitable point of entry, however, more superior or inferior positions may be preferred to allow passage of the distal end of a lead along a significant region of the ventricles and atria by passing in a single direction.

In the example shown, illustrative intercostal access locations are shown at relatively inferior positions 330, 332, and more superior positions 340, 342. In either case, access may be had using ultrasound guided needle insertion. Again, the access method may resemble the Seldinger technique, though in this case the muscle in the intercostal space would first be traversed. A needle may be used to establish puncture using ultrasound guidance, with a guidewire passed therethrough. Once the puncture is made and the guidewire is in the desired blood vessel, the needle is removed, keeping the guidewire in place, and an appropriately sized introducer sheath (optionally including a dilator) is placed over the guidewire.

The alternative in FIG. 6B allows access from either superior or inferior positions while preserving the upper thoracic vasculature. Such an access position may be labeled a parasternal access position. An advantage over the approach of FIG. 6A is that the use of a suture sleeve attachment with FIG. 6B would occur on the fascia over the ribcage near the intercostal access point, making suture sleeve use easier and avoiding movement between the point of venous system entry and the point of fixation. On the other hand, a user may be more comfortable accessing the veins at a location where the ribs and intercostal muscles do not interfere; thus, each of the various approaches herein has advantages and disadvantages relative to one another.

Figure 7:
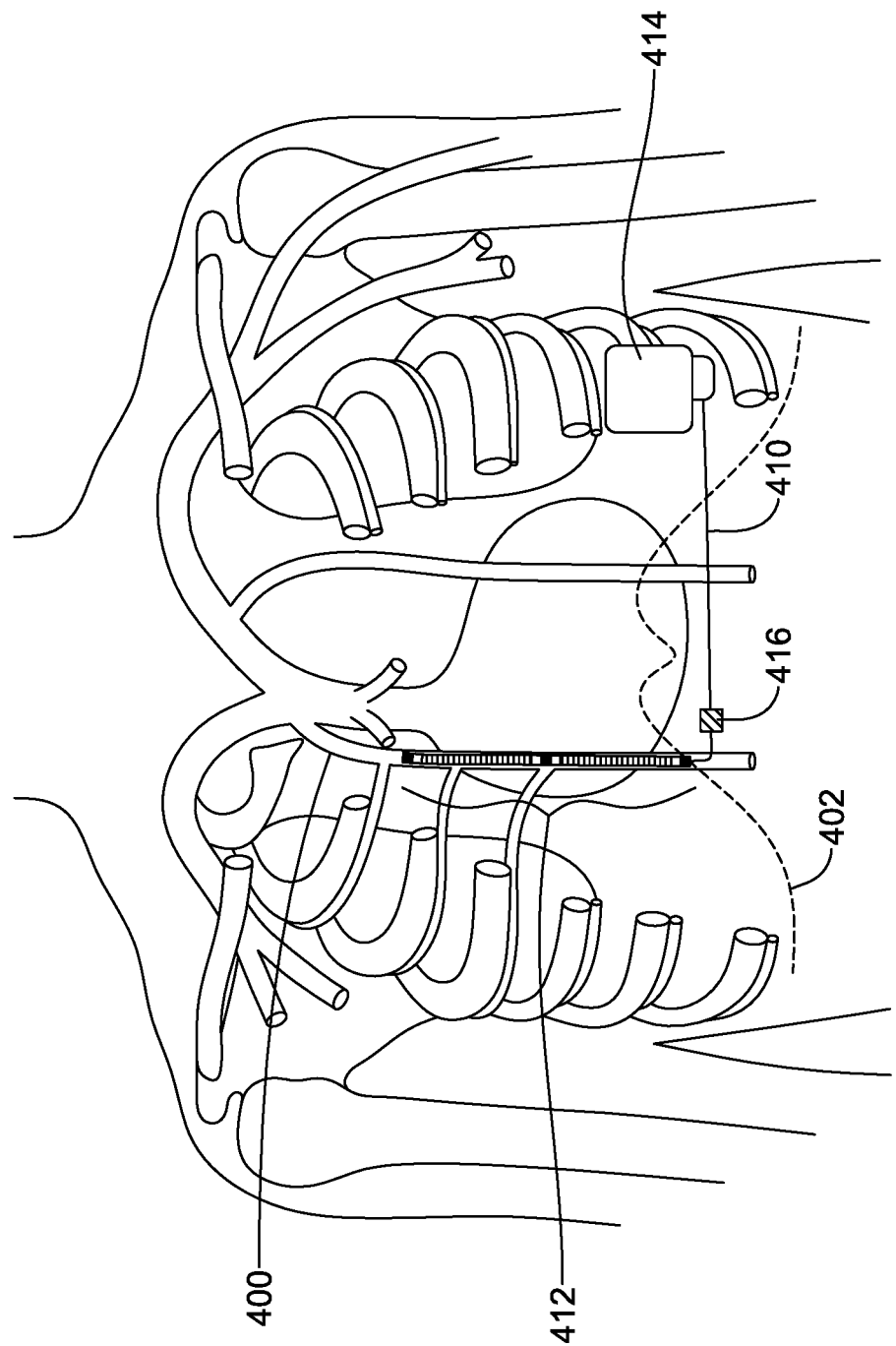
FIG. 7 shows implantation from an inferior position in a right ITV.

FIG. 7 shows implantation from an inferior position in an ITV. In this example, the right ITV 400 has been accessed by introduction through the superior epigastric vein from a location inferior to the rib margin 402. An implantable device has been placed including a lead 410 having a distal electrode structure 412 and a canister 414, with the canister 414 placed at approximately the left axilla. The canister 414 may be placed as desired, for example at the anterior axillary line, the midaxillary line, or in the posterior axillary line.

In the illustration, a suture sleeve is shown at 416 and is used to fixate the lead 410, for example, to the subcutaneous fascia. For placement, the right ITV 400 is accessed as described above, and a tunnel is established between the left axilla and the access location such as along a portion of the inframammary crease. The lead 410 may, in this case, be relatively stiff to assist in keeping it emplaced in the patient as shown, if desired. Various designs are shown herein for the lead as well, including tines, hooks, curvature or bias of the lead, and inflatable or expandable structures. In the example of FIG. 7, a left axillary canister location is shown; a right sided, pectoral or subclavicular left or right position may be used instead, in combination with the right ITV placement 400 or, alternatively a left ITV placement.

Figure 15:
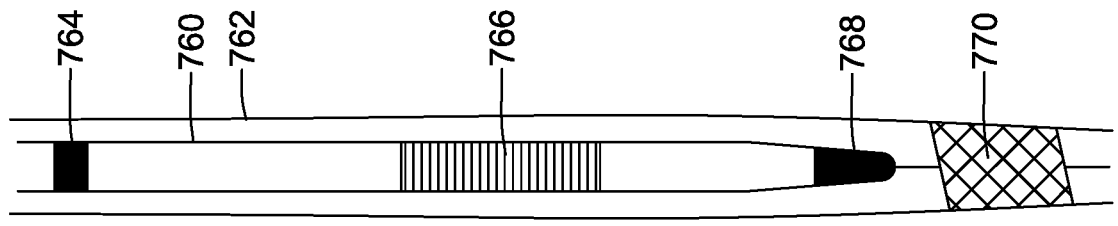
Figure 16:
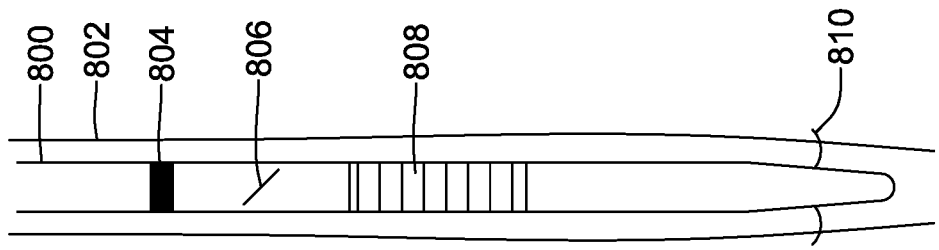

During implantation, a sheath may be provided over the lead 410, or at least a portion thereof, to retain or restrain a fixation apparatus or shape for the flexible lead, such as a 2 or 3 dimensional curvature (see FIGS. 10-11), tines (see FIG. 12), an expandable member (see FIG. 15), or hooks or a side-extending engagement structure (see FIG. 16). A stylet may be placed through the lead 410, or a portion thereof, to retain a straight shape during implantation; upon removal of the stylet, a curvature (see FIGS. 10-11) may then be released for securing the lead 410 in place.

The lead 410 may include additional or different electrodes than those shown. For example, another coil electrode may be placed on a more proximal portion of the lead 410 to reside along the inframammary crease in a location between the canister 414 and the point of access into the superior epigastric vein. The additional coil at this location may be used for defibrillation or other therapy purposes, or for sensing. If desired, second or more leads may also be placed.

Figure 8A:
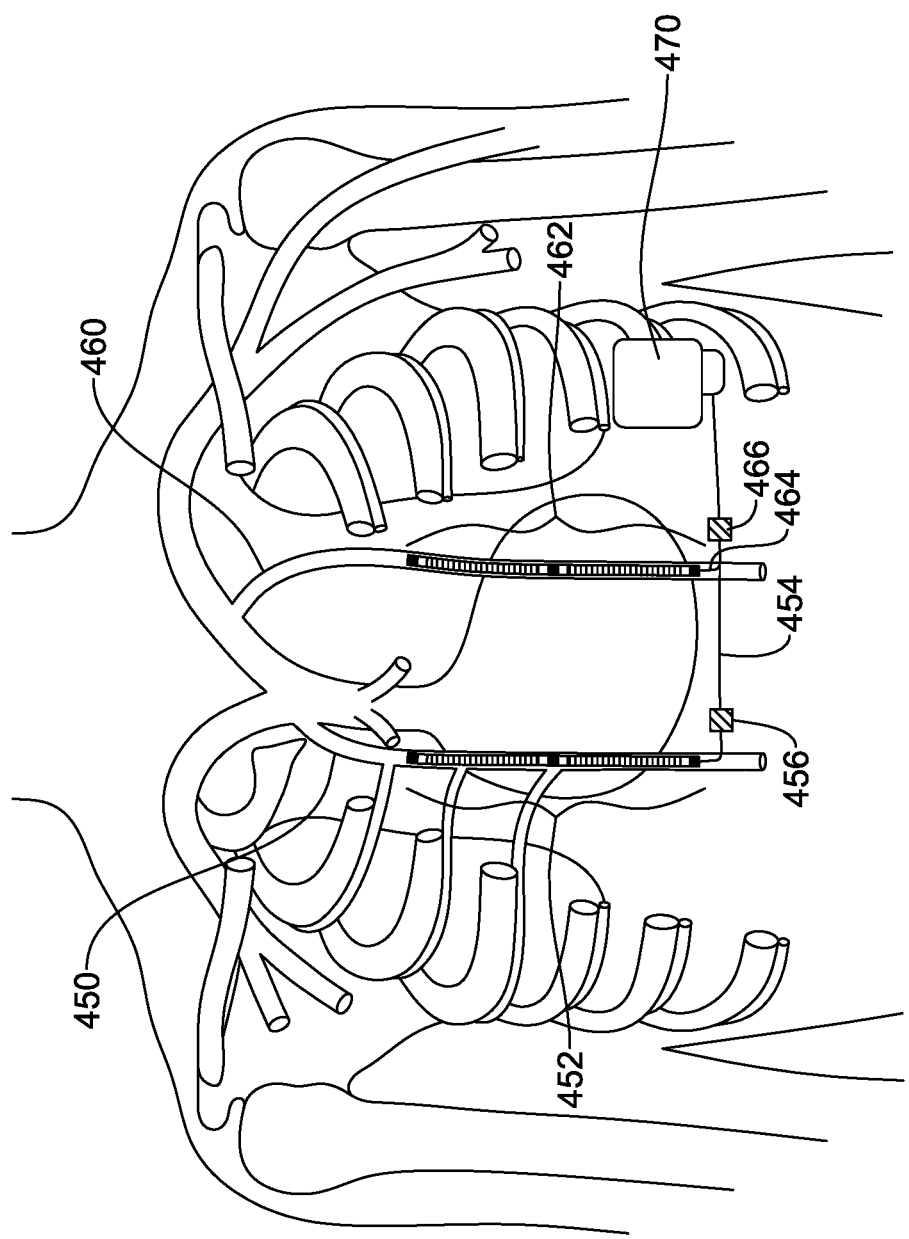
FIG. 8A shows implantation from an inferior position in both ITVs.

FIG. 8A shows implantation from an inferior position in both ITV. In this example, the right ITV 450 is shown with the electrode structure 452 on a distal end of a lead 454 disposed therein. A suture sleeve 456 secures the lead 454. The lead 454 includes a second branch that enters the left ITV 460 with a distal electrode structure 462 disposed therein. A second suture sleeve 466 optionally secures the lead 454 at a second location. A canister for the system is shown implanted in the left axilla. As noted above, the point of access to each of the right and left superior epigastric veins, in order to enter the right and left ITV 450, 460, may be placed close to the xiphoid process at the, and/or at or near paraxiphoid window, near the $7^{th}$ rib margin. More inferior access to the superior epigastric veins may be used if desired.

Figure 8B:
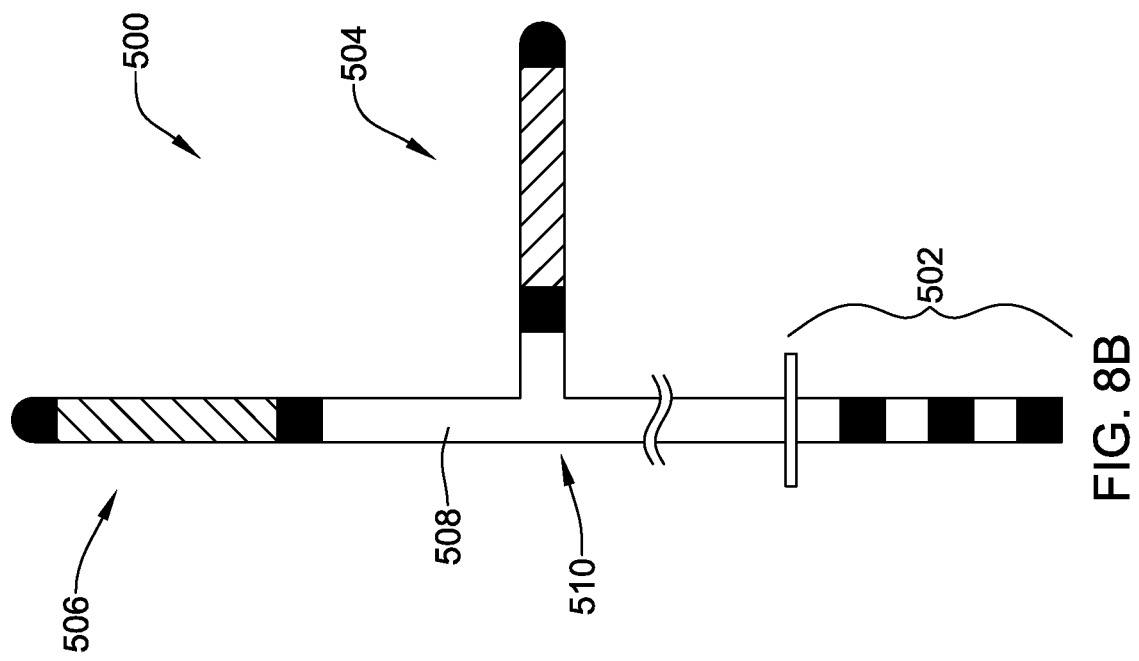
FIG. 8B shows an illustrative lead that may be used in the implantation configuration of FIG. 8A.

FIG. 8B shows an illustrative lead that may be used in the implantation configuration of FIG. 8A. The illustrative lead 500 includes a proximal plug structure shown at 502, with a split at 510, from which a shorter branch having an electrode structure 504 extends, and a longer branch 508 continuing in the axial direction to another electrode structure 506. The design is illustrative and not intended to be limiting. In another example, two separate leads may be used, rather than one integrated lead.

As shown, each electrode structure 504, 506 includes a coil electrode flanked with two sensing electrodes; other combinations of electrodes may be used. Each electrode may be electrically connected to a single contact on the plug 502 or, if desired, subsets of electrodes may be ganged together relative to a single contact on the plug 502. The distal portion may include a fixation apparatus or shape for the flexible lead, such as a 2 or 3 dimensional curve (see FIGS. 10-11), tines (see FIG. 12), an expandable member (see FIG. 15), or hooks or a side-extending engagement structure (see FIG. 16).

Figure 9:
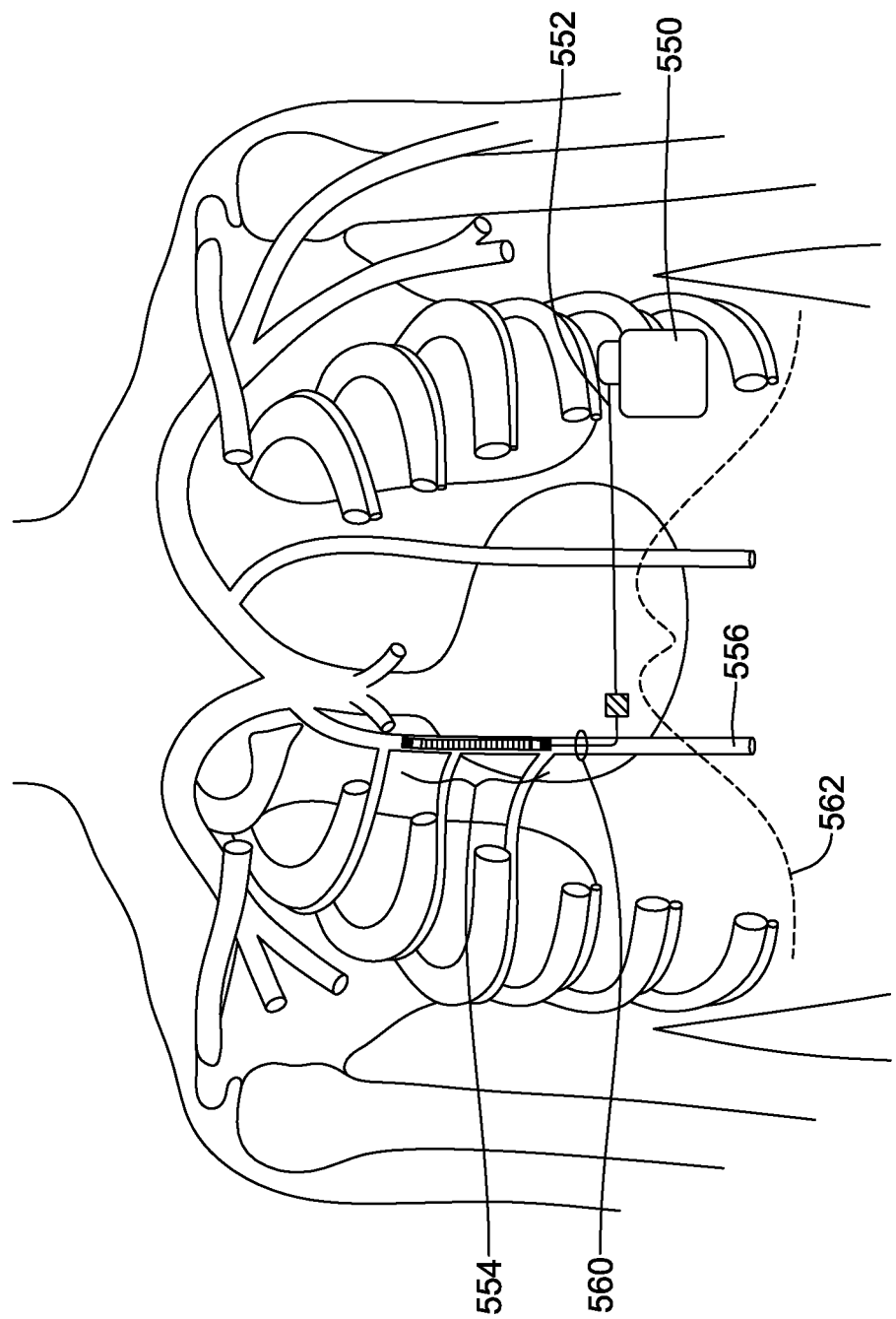
FIG. 9 shows implantation using an intercostal access to the right ITV.

FIG. 9 shows implantation using an intercostal access to an ITV. In this example, an implantable system having an implantable pulse generator 550 and lead 552 with distal electrode structure 554 has been emplaced in a patient. The right ITV 556 is accessed using an intercostal access point at 560.

The intercostal access 560 may be achieved by inserting a needle, preferably under guidance such as by the use of an ultrasound guided needle, into a chosen intercostal space, preferably low on the ribcage and near the sternum, through the muscle of the intercostal space and into the right ITV 556. A guidewire can be passed through the needle and an introducer sheath passed over the guidewire after removal of the needle. Other techniques may be used instead, and other access points may be selected.

A suture sleeve may be used to secure the lead 552 over the ribcage as desired. The lead 552, as with all other implanted leads shown herein, may include a fixation structure such as bends or curves along its distal length, or tines, hooks or expandable members at its distal end to secure its position within the ITV 552.

FIGS. 10-19 illustrate various lead designs. These leads may be manufactured of any suitable material and by any suitable manner. For example, numerous polymers are known for lead manufacture. Internal longitudinal or lateral support members, such as braids, core wires, etc. may be provided. Extrusion or molding may be used. Internal conductors may be formed of any suitable material (stainless steel, titanium, gold, silver, or any other conductive material may be used) and may take any suitable form, such as simple wires, coated wires, braided or wound wires, drawn wires, and/or drawn filled tubes, or other structures. The leads may include on all or a portion thereof various coatings such as an anti-microbial coating to reduce the likelihood, severity, and/or progression of infection. Some illustrative lists for such design details follow later in the disclosure.

Figure 10:
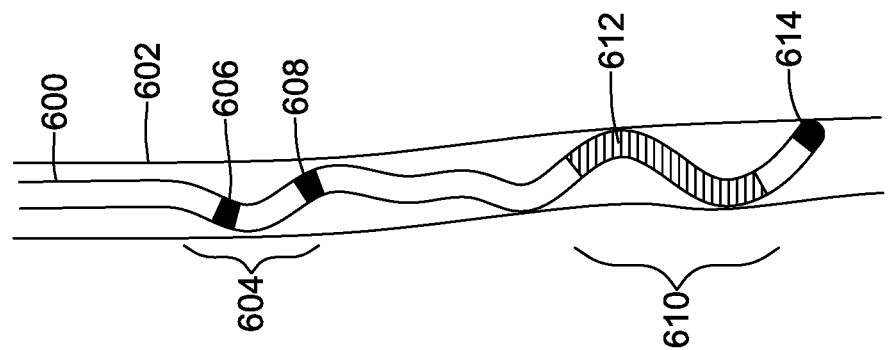

FIG. 10 shows an illustrative lead structure. A lead 600 is shown within a blood vessel 602, which may be an ITV. The lead may include ring electrodes illustrated at 606, 608, and a tip electrode 614, as well as a coil electrode at 612. Regions of curvature area shown at 604, and at 610. A single curvature may be provided instead. The curvature may be two-dimensional or three-dimensional. A two dimensional curvature may take the form, generally, of a zig-zag design, for example. Several embodiments may use a three dimensional curvature such as a pigtail or helix, for example.

In one example, the distal tip 614 is implanted inferior relative to the rest of the lead, such that the coil 612 is adjacent or level with the patient's ventricles. In another example, the distal tip is implanted superior relative to the rest of the lead, such that the coil 612 is adjacent or level with the patient's atria. In another example, the position of coil 612 is switched with the position of ring electrode 608, such that if implanted with the tip 614 superior relative to the rest of the lead, the tip 614 would be at about the level of the atria (or higher), while the coil 612 would be adjacent to or level with the ventricles.

Figure 11:
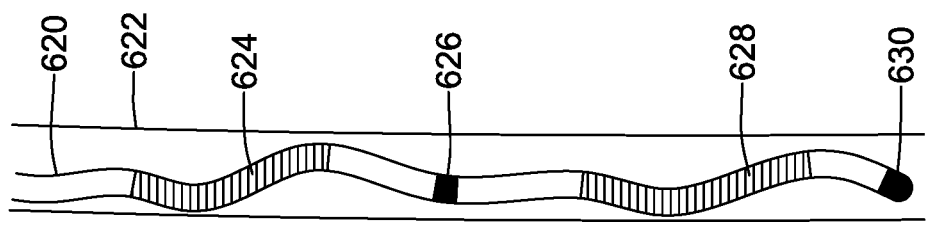

FIG. 11 shows another example. A lead 620 is shown within a blood vessel 622, which may be an ITV. The lead may include ring electrode 626 and a tip electrode 630, as well as coil electrodes 624, 628. An additional ring electrode may be placed proximal of the coil electrode 624, as shown above in FIG. 5, if desired. With this example, the coils 624 may be spaced and positioned such that one is level with the ventricles and the other is level with the atria when implanted with the tip 630 either superior or inferior. As with FIG. 10, FIG. 11 shows that the lead has several areas of curvature.

In FIGS. 10 and 11, the curvature may be assumed by the lead in several ways. In an example, the lead includes a shape memory material and is generally straight and flexible until implanted in the body; after a few minutes to warm up, the shape memory material assumes the shape shown. In another example, a stylet is placed inside the lead during implantation to retain a generally straight shape, and the lead assumes the curved shape shown when the stylet is removed. In another example, an outer sheath is used to retain the lead until it is implanted with removal of the outer sheath allowing the lead to assume a desired shape. Combinations may be used as well; for example, a lead may include a shape memory portion or material or support structure, and may be implanted with the aid of a stylet and outer sheath to retain a low profile for implantation and then, once released by removal of the stylet and sheath, the shape memory material exerts forces to assume the shapes shown. Though not shown, curvature may be used for secure placement of any of the leads shown in FIGS. 12-18, if desired.

Figure 12:
FIGS. 10-19 illustrate various lead designs.

FIG. 12 shows another example. Here, a lead 650 is shown inside a blood vessel 652, which may be the ITV. First and second ring electrodes are shown at 654, 656, and third and fourth ring electrodes are shown at 658, 660. Tines for fixation are shown at 662. The ring electrodes may be placed such that if the tines 662 are superior relative to the rest of the lead, electrodes 658, 660 would be level with the atria, and electrodes 654, 656 would be level with the ventricles. This may facilitate separate atrial and ventricular sensing and/or pacing channels. A coil electrode may also be provided.

In one example, a lead as shown in FIG. 12 is implanted in the left ITV while a separate lead is implanted in the right ITV, with the right ITV comprising a defibrillation coil electrode, with an active canister defibrillator implanted in the left axilla. This approach would allow sensing (and optionally, pacing) directly over the heart using the ring electrodes 654, 656, 658, 660, with defibrillation delivered across the majority of the myocardium between the right-sided coil electrode and the left sided canister.

Figure 13:
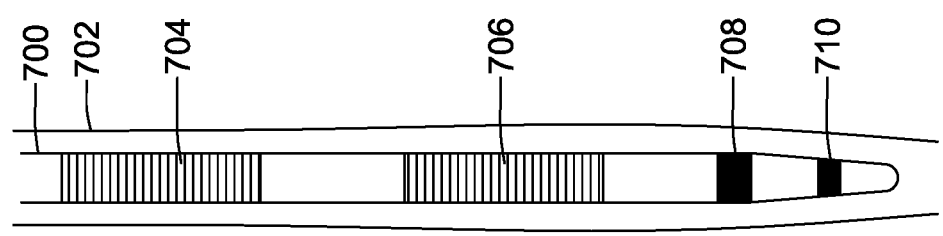

FIG. 13 shows another example. Here a lead 700 is implanted in a blood vessel 702 which may be an ITV. A first coil is shown at 704 and a second coil is shown at 706, with two distally located ring electrodes. If desired, the lead may taper as shown, though a fully cylindrical lead may be used instead. The taper may be useful during implantation to facilitate easier access through venous valves, particularly for insertions from superior to inferior, where the direction of insertion is counter to blood flow and hence valve structure. Curves or tines may be added, as well as other fixation features noted herein.

Figure 14:
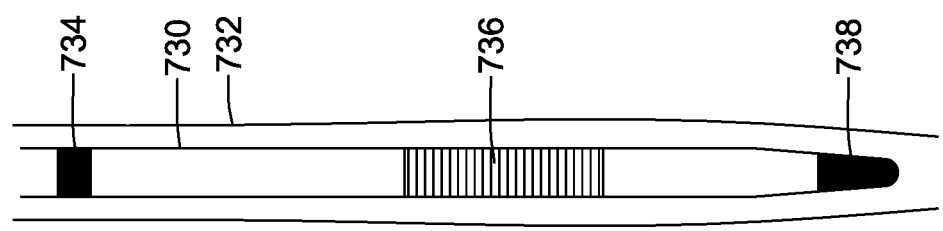

FIG. 14 shows another example. In this example, a lead 730 is shown inside of a blood vessel 732 which may be an ITV. A proximal ring electrode is shown at 734 and a coil at 736, with a distal tip electrode at 738. Curvature or tines may be added, as well as other fixation features noted herein.

FIG. 15 shows another example. Here, the lead is much as in FIG. 14, with lead 760 shown inside a blood vessel 762 which may be a ITV, and with a proximal ring electrode 764, coil electrode 766, and distal tip electrode 768. However, now, an expandable member, such as a stent 770 is shown distal to the distal tip electrode 768. For example, a self-expanding stent 770 may be provided and carried within the distal tip electrode 768 until a desired position is reached for the stent 770. Such positioning may be determined using, for example, fluoroscopy. The proximal end of the lead may include a release mechanism, such as a control wire that can be advanced relative to the lead body, to push the stent 770 beyond the distal tip electrode 768 where it can then release. Self-expanding stents are well known in the art and may include, for example, spring-like structures. The stent 770 may include coatings designed to prevent thrombus from forming thereon and/or to encourage angiogenesis to best engage the venous wall. For removal, the connection to the stent 770 may be cut, for example, to leave the stent 770 in place as the rest of the lead is removed. Optionally the stent may be later removed using, for example, a stent retriever.

FIG. 16 shows another example. Here, a lead 800 is shown in a blood vessel 802 which may be an ITV. A proximal coil electrode is shown at 804. Distal of the proximal coil electrode (though any suitable location, more proximal or more distal, may be chosen), a side-engaging member is shown at 806. For example, engaging member 806 may be an arm, coil, hook, or tine that expands outward when actuated from the proximal end of the lead. Once the lead is in a desired position, engaging member 806 may be actuated to secure the lead in place.

The lead 800 is also shown with a coil electrode at 808. Finally, at the distal tip of the lead, a plurality of hooks are shown for engaging the walls of the blood vessel 802. The engaging member 806 or hooks 810 may be coated as desired for anti-thrombogenic or pro-angiogenic reasons, for example.

Figure 17:
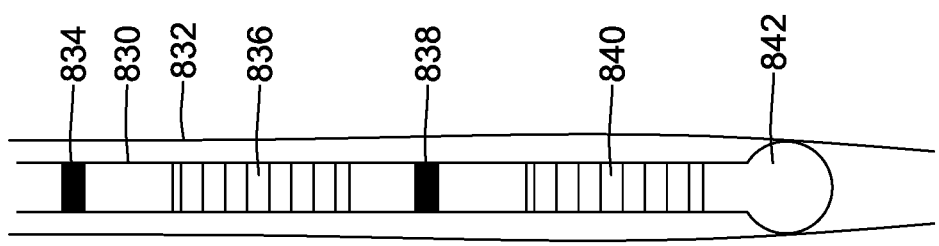

FIG. 17 shows another example. Here, a lead 830 is shown inside of a blood vessel 832 which may be an ITV. A plurality of electrodes are shown including a ring electrode 834, coil electrode 836, ring electrode 838, and coil electrode 840. At the distal end of the lead is an expandable member, such as a balloon, which may be inflated to secure the lead in place. It should be noted that the ITV is a blood vessel which, if occluded, will not necessarily cause harm to the patient as contralateral accommodation occurs readily. The balloon 842 may be expanded using inflation pressure, for example. A compliant or non-complaint material may be used the balloon. Rather than a balloon, an expandable sponge-type member that increases in volume once sufficiently wetted may be used instead.

Figure 18:
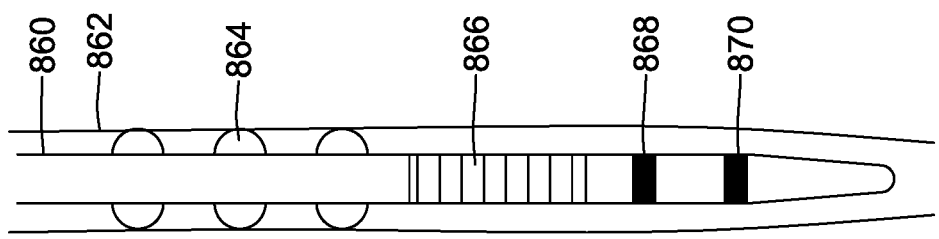

FIG. 18 shows another example. In this example, the lead 860 is shown in a blood vessel 862 which may be an ITV. This example includes a plurality of lobes 864 which hold the lead 860 in place inside the blood vessel 862. For example, the lobes may self-expand on removal of an outer delivery sheath or catheter, or the lobes may be expanded by movement of an outer shell of the lead relative to an inner shell. A coil electrode is shown at 866 and ring electrodes are shown at 868, 870.

Figure 19:
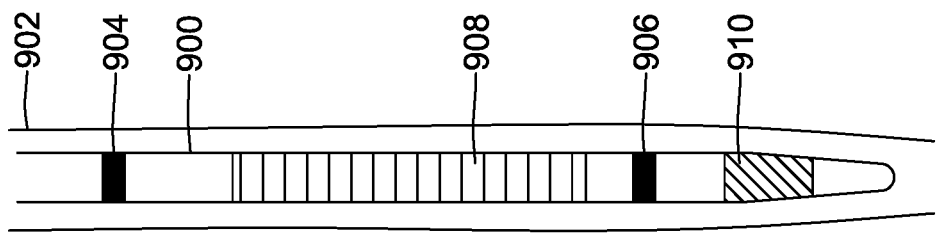

FIG. 19 shows another example. A lead 900 is shown within a blood vessel 902, which may be an ITV. The lead may include ring electrodes illustrated at 904, 906, a coil electrode 908, and a motion detector, sound sensor, and/or accelerometer 910. If so provided, an accelerometer 910 may provide a clinician and/or the canister with heart motion data as well as heart sound data (e.g., the S3 heart sound). Either or both the heart motion data and the heart sound data may be used to provide heart failure status information.

The examples of FIGS. 10-19 are merely illustrative. Some examples may omit any fixation on the portion of the lead that extends into the blood vessel, and may instead rely on fixation using a suture sleeve subcutaneously placed as shown in certain of the above examples. In some examples, a relatively stiff lead may be used, as repeated flexion is not necessary when implanted in the ITV in the same manner as is the case inside the heart. A stiff lead is believed to be less likely to migrate.

Figure 20:
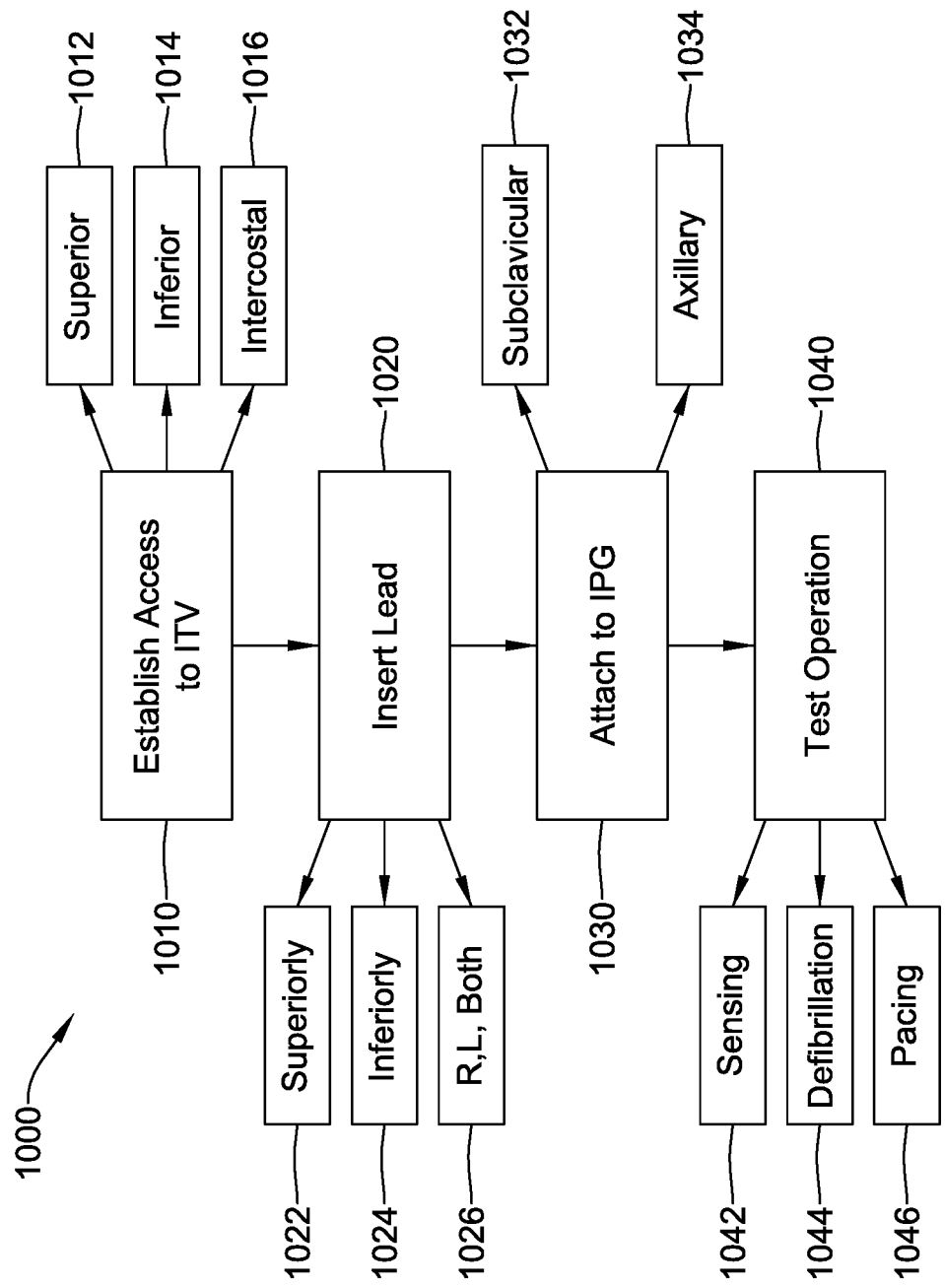
FIG. 20 is a block flow diagram for an illustrative method.

FIG. 20 is a block flow diagram for an illustrative method for providing a cardiac stimulus system to a patient. As shown at 1000, the method comprises establishing access to the ITV 1010, inserting a lead in the ITV 1020, attaching an IPG to the lead 1030, and performing test operations 1040.

For example, establishing access to the ITV 1010 may include accessing from a superior position 1012 such as by entering the subclavian vein and passing through the ostium of the ITV in the brachiocephalic vein. In another example, establishing access to the ITV 1010 may include accessing from an inferior position 1014 such as by entering the superior epigastric vein and passing superiorly therefrom into the ITV. In some examples, access via locations 1012, and 1014 may include accessing via a second blood vessel such as by accessing superiorly 1012 by way of the subclavicular vein and brachiocephalic vein, or accessing inferiorly 1014 through the superior epigastric vein. In still another example, establishing access to the ITV may include accessing in an intercostal space 1016 such as by penetrating an intercostal space and entering the ITV using a Seldinger technique.

In an example, inserting a lead 1020 may include insertion superiorly 1022, such as by starting in an inferior position 1012 inferior to the lower rib margin or intercostally 1016 from an inferior intercostal location, and advancing the lead in a superior direction. For another example, inserting a lead 1020 may include insertion inferiorly 1024 that is, starting at a superior location 1014 or at a superior intercostal location 1016, and advancing the lead in an inferior direction. In either such example, the right ITV, left ITV, or both ITV vessels may be used, as indicated at 1026.

Other vessels and implanted lead locations may also be used (such as having a lead in the azygos vein, an intracardiac lead, and/or a subcutaneous lead) or additional devices such as a separately implanted leadless cardiac pacemaker may be included as well. In a further example, one or more of the transverse veins that flow into the ITV may be used for placement of an electrode or lead. For example, upon accessing an ITV, a physician may further access and emplace a lead or electrode into one of the anterior intercostal veins which run along the intercostal spaces of the anterior chest.

In an example, attaching to an IPG may include attaching to a canister located in a subclavicular location 1032, historically a common place to put an implanted canister for a transvenous defibrillator or pacemaker. In another example, attaching to an IPG may include attaching to a canister located in an axillary position 1034, such as that used with the S-ICD System. Other IPG locations may be used. Attachment may be directly to the IPG or to a splitter, yoke, or lead extension, if desired.

In an example, test operation 1040 may be used to verify one or both of device functionality and efficacy. For example, sensing operations 1042 may be tested and configured to check for adequate signal availability, for example, or by setting gain, filtering, or sensing vector selection parameters. Defibrillation operations 1044 may be tested by inducting an arrhythmia such as a ventricular fibrillation to determine whether the device will sense the arrhythmia and, if the arrhythmia is sensed, to ensure that the device can adequately provide therapy output by delivering defibrillation at a preset energy. Defibrillation testing 1044 may include determining for a given patient an appropriate defibrillation threshold, and setting a parameter for therapy delivery at some safety margin above the defibrillation threshold.

Prior transvenous systems would typically deliver up to 35 Joules of energy at most, with storage of up to 40 Joules of energy, using peak voltages in the range of up to nearly 1000 volts. The S-ICD System can deliver up to 80 Joules of energy, with 65 Joules often used for in-clinic system testing, with a peak voltage in the range of 1500 volts. The ITV location may facilitate energy levels similar to those of traditional transvenous systems (5-35 Joules, approximately), or may be somewhat higher (5 to about 50 joules, for example), or may still be higher (10 to about 60 joules, for example). Pacing thresholds may also be closer to those for traditional transvenous systems than the more recent S-ICD System.

In an example, pacing testing operation 1046 may include determining which, if any, available pacing vectors are effective to provide pacing capture. If desired, parameters may be tested as well to determine and optimize settings for delivery of cardiac resynchronization therapy. This may include testing of pacing thresholds to optimize energy usage and delivery, as well as checking that adverse secondary effects, such as patient sensation of the delivered pacing or inadvertent stimulation of the phrenic nerve, diaphragm or skeletal muscles are avoided.

In some cases, the left and/or right ITV may be used to access an intercostal vein. Electrodes may be placed in the intercostal veins in addition to or in place of electrodes in the ITV to increase the number of lateral and posterior defibrillation vectors which may further reduce defibrillation thresholds. From such a position, beneath the rib cage, the amount of energy required for defibrillation and pacing efficacy would logically be lower than outside of the sternum and/or rib cage, since the ITV location is closer to the heart and bone is generally not a very good conductor of electrical energy, at least when speaking in terms of the tissues in the human body.

Figure 21:
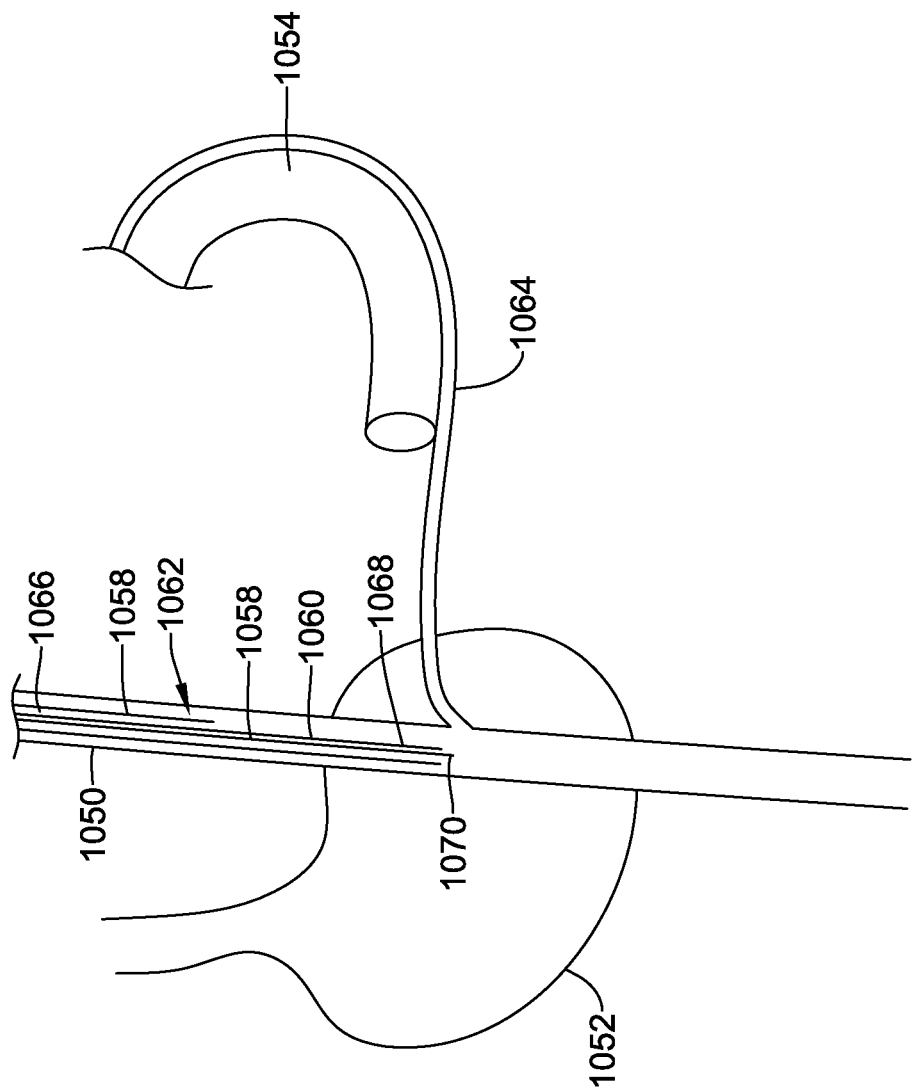
FIGS. 21-25 illustrate a method of implanting a lead in an intercostal vein and the ITV.

FIGS. 21-25 illustrate a method for placing a lead in an intercostal vein. While the method is described using a superior approach, it is contemplated that the superior epigastric vein may be used to access the intercostal veins using an inferior approach as described above. FIG. 21 is an anterior view of a portion of an illustrative method for placing a lead in the intercostal vein through the left and/or right ITV. Referring now to FIG. 21, in this example, a patient is shown in an anterior lateral view with relevant elements shown in isolation for clarity purposes. The ITV is shown at 1050 (item 1050 may be the left or right ITV), passing generally over the heart 1052 and beneath the ribs 1054. For clarity, only a single rib 1054 is illustrated and portions have been removed to better illustrate the ITV 1050 and other anatomical features. Access to the ITV 1050 may be achieved using any of the methods described above (e.g., superior access, inferior access, cut-down, intercostal access, etc.).

A guidewire 1056 is advanced through the ITV 1050 to a desired location adjacent to the heart 1052 and an intercostal vein 1064. The guidewire 1056 may be the same as used in gaining initial access to the vessel (if one is used to gain access), or may be a different guidewire. In some instances, the guidewire 1056 may have a diameter in the range of 0.030 to 0.040 inches (0.762 to 1.016 millimeters), or about 0.035 inches (0.889 millimeters). In other instances, the guidewire 1056 may have a diameter in the range of 0.009 to 0.019 inches (0.229 to 0.483 millimeters), or about 0.014 inches (0.356 millimeters). These are just examples. The size of the guidewire 1056 used may be dependent on the size of the device to be advanced over the guidewire 1056.

A guide catheter or sheath 1058 is advanced over the guidewire 1056. The guide catheter, or outer catheter, 1058 may include a curved distal end region 1062 to facilitate navigation through the vasculature. In some instances, the curved distal end region 1062 may have a curve of 90° or greater. Although, the curve can be less than 90°, as desired. In other instances, the distal end region 1062 may be deflectable (e.g., through pull wires or other deflection mechanism) to allow the user to deflect (e.g., bend) the catheter 1058 as needed. The catheter 1058 may be positioned or seated within the ITV 1050.

Figure 22:
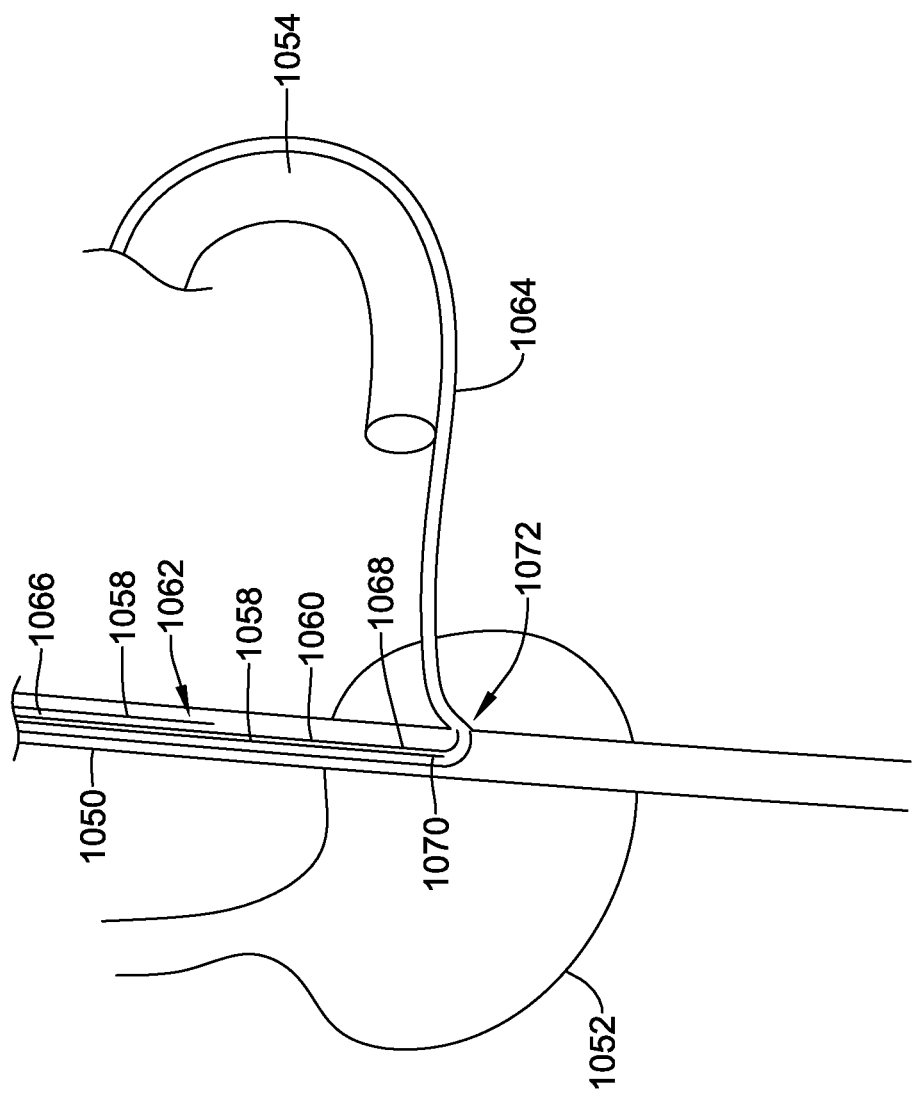

An inner catheter 1060 is then advanced within the lumen 1066 of the outer catheter 1058 and over the guidewire 1056. The inner catheter 1060 may include a curved distal end region 1068 to facilitate navigation through the vasculature. In some instances, the curved distal end region 1068 may have a curve of 90° or greater. Although, the curve can be less than 90°, as desired. In other instances, the distal end region 1068 may be deflectable (e.g., through pull wires or other deflection mechanism) to allow the user to deflect (e.g., bend) the catheter 1060 as needed. In some cases, the guidewire 1058 may be sufficiently rigid to maintain the distal end region 1068 in a substantially straight configuration. The inner catheter 1060 may be advanced distally beyond the distal end 1070 of the guidewire 1058 such that the distal end region 1068 can assume its predefined curved configuration, or be deflected into a curved configuration, as shown in FIG. 22. The curved distal end region 1068 may be used to identify the opening 1072 of an intercostal vein 1064 (e.g., a junction between an intercostal vein 1064 and the ITV 1050).

Figure 23:
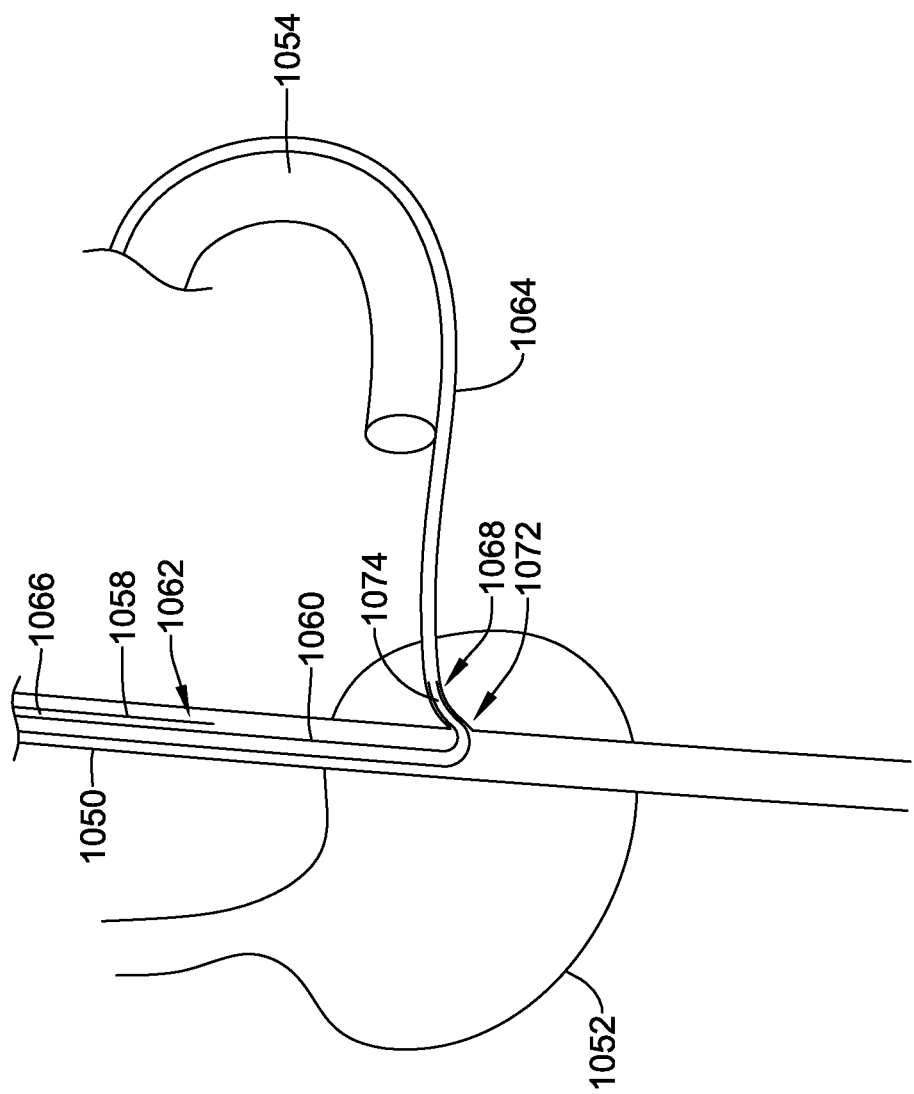

The distal end region 1068 of the inner catheter 1060 may be further advanced into the intercostal vein 1054 to cannulate the intercostal vein, as shown in FIG. 23. The guidewire 1056 is also removed to allow for passage of a lead 1076 through a lumen 1074 of the inner catheter 1060. Various leads with a combination of electrodes and/or sensors may be delivered through the lumen 1074 of the inner catheter 1060.

Figure 24:
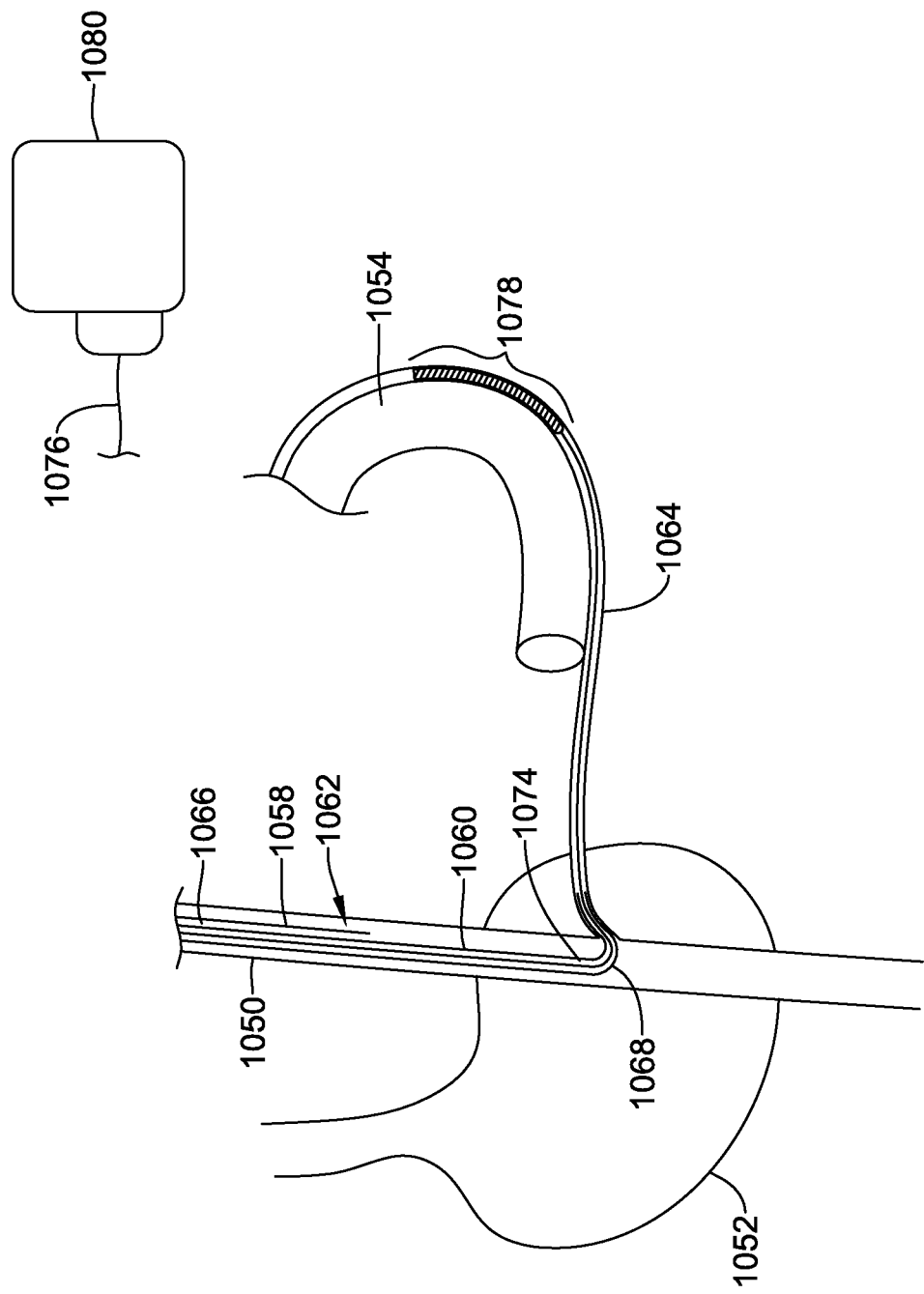

FIG. 24 shows implantation of an implantable cardiac stimulus device in the intercostal vein 1064, with the inner catheter 1060 and guide catheter 1058 still in place. The system includes an implantable pulse generator 1080 which may be placed in a subclavicular location, at the anterior axillary line, the midaxillary line, or in the posterior axillary line (or any other suitable position, as desired). The pulse generator 1080 may be placed as shown in U.S. patent application Ser. No. 15/667,221, titled PACEMAKERS FOR IMPLANT IN THE INTERNAL THORACIC VASCULATURE WITH COMMUNICATION TO OTHER IMPLANTABLE DEVICES, the disclosure of which is incorporated herein by reference.

A lead 1076 passes into the intercostal vein 1064 through the ITV 1050. The lead 1076 may be passed laterally and posteriorly through the intercostal vein 1064. In some cases, the lead 1076 may extend through the anterior intercostal vein and into the posterior intercostal vein. Positioning the lead 1076 in a more lateral and/or more posterior position relative to the heart 1052 may further reduce the defibrillation thresholds relative to a lead 1076 positioned closer (laterally and/or anteriorly) to the heart. While the lead 1076 is described as being advanced without the guidewire 1058, the lead 1076 may be delivered to the intercostal vein 1064 with or without the use of a guidewire using any of the delivery mechanisms and methods described herein with respect to delivery in the ITV.

In the example, the lead 1076 includes a coil electrode as shown at 1078. The coil electrode 1078 may be a high voltage coil that may also serve as a pacing anode. However, any of the lead designs described with respect to FIGS. 5 and 10-19 may be used. Further, while an anchoring mechanism is not explicitly shown, the lead can be fixated in the vasculature using various means such as tines, hooks, biases, T-bar tethers, and other means. In addition to the engaging members described herein some illustrative additional anchoring mechanisms are discussed in US PG Patent Application Pub. No. 20170021159, titled SUBSTERNAL PLACEMENT OF A PACING AND/OR DEFIBRILLATING ELECTRODE, as well as US PG Patent Application Pub. No. 20170095657, titled FIXATION DEVICE FOR A SUBCUTANEOUS ELECTRODE, the disclosures of which are incorporated herein by reference. The proximal end of the lead 1076 may be connected to an implantable pulse generator 1080.

In some cases, the lead 1076 may be placed on the left side of the patient. In other examples, the right side of the patient may instead or in addition be accessed, including the right ITV. Access to the right ITV may be achieved by advancing a guide catheter and/or guidewire from in any of the manners described herein.

In some examples, a lead 1076 may be placed in intercostal veins from the left and right ITVs. In such an instance, a lead 1076 is delivered through each of the left and right ITV to an intercostal vein in a manner similar to that described with respect to FIGS. 21-24. Pacing between right and left side lead placements may be performed to target specific chambers or chamber combinations, or sensing may be performed using one pair of electrodes with therapy delivery using a different pair of electrodes to achieve resynchronization or other desirable effect.

Figure 25:
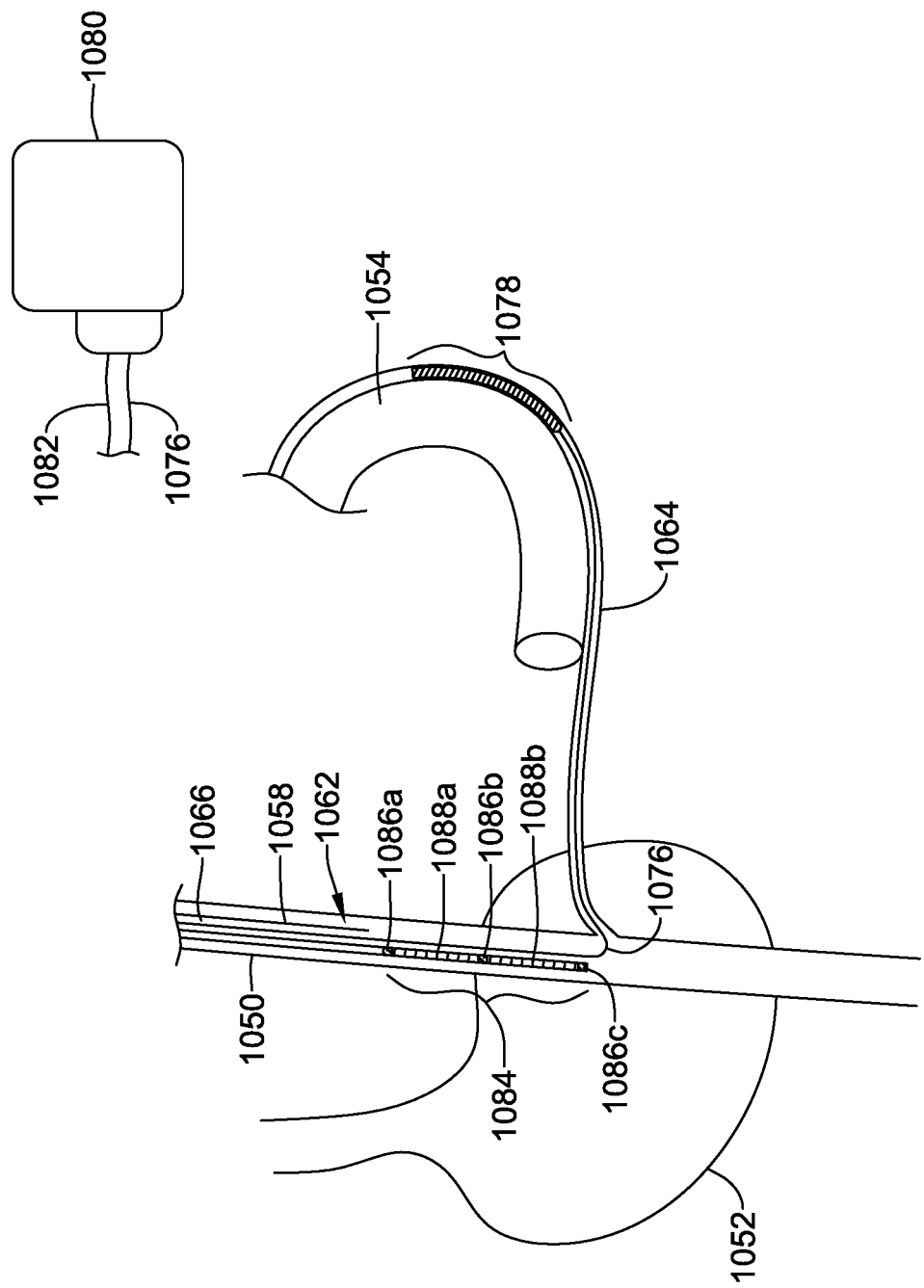

After placement of the first lead 1076, the inner catheter 1060 may be completely removed or slightly retracted to allow for placement of a second lead 1082 in the ITV 1050, as shown in FIG. 25. The lead 1082 may be advanced in a similar manner to the lead 1078 described above. The guidewire 1056 and the catheters 1058, 1060 (if still in the vessel) may be removed after placement of the lead 1082.

In the example, the second lead 1082 includes a multi-electrode distal structure as shown at 1084. However, any of the lead designs described with respect to FIGS. 5 and 10-19 may be used. Further, while an anchoring mechanism is not explicitly shown, the lead can be fixated in the mediastinum using various means such as tines, hooks, biases, T-bar tethers, and other means. In addition to the engaging members described herein some illustrative additional anchoring mechanisms are discussed in US PG Patent Application Pub. No. 20170021159, titled SUBSTERNAL PLACEMENT OF A PACING AND/OR DEFIBRILLATING ELECTRODE, as well as US PG Patent Application Pub. No. 20170095657, titled FIXATION DEVICE FOR A SUBCUTANEOUS ELECTRODE, the disclosures of which are incorporated herein by reference. In some cases, the leads 1076, 1082 may be combined into or connected to a single wire for connection to the pulse generator 1080, although this is not required.

In some cases, the lead 1082 may be placed on the left side of the patient. In other examples, the right side of the patient may instead or in addition to be accessed, including the right ITV. Access to the right ITV may be achieved by advancing a guide catheter and/or guidewire from in any of the manners described herein.

In some examples, a lead 1082 may be placed in both the left and right ITVs. In such an instance, a lead 1082 is delivered through each of the left and right ITV in a manner similar to that described with respect to FIG. 25. Pacing between right and left side lead placements may be performed to target specific chambers or chamber combinations, or sensing may be performed using one pair of electrodes with therapy delivery using a different pair of electrodes to achieve resynchronization or other desirable effect.

In this example, the lead structure includes a proximal coil 1088A separate from a distal coil 1088B. The coils 1088A/B and canister 1080 may serve as therapy delivery electrodes. As such there may be multiple therapy vectors such as between coil 1088A and coil 1088B, between either of coils 1088A and 1088B and the canister 1080, or between a combination of two of the three therapy electrodes 1088A, 1088B and canister 1080, and the third such electrode, such as by linking coils 1088A and 1088B in common as the anode or cathode relative to the canister 1080. Alternatively, or additionally vectors may be between either of coils 1088A and 1088B and the coil electrode 1078 in the intercostal vein 1064.

A plurality of ring electrodes may be provided as shown at 1086A, 1086B, and 1086C. Electrode 1086C may also or instead be a tip electrode. Electrodes 1086A/B/C may serve as sensing electrodes. The coils 1088A, 1088B may also serve as sensing electrodes. These various electrodes may be used for sensing cardiac signals in various combinations using, for example, methods and circuitry discussed in U.S. Pat. No. 7,783,340, titled SYSTEMS AND METHODS FOR SENSING VECTOR SELECTION IN AN IMPLANTABLE MEDICAL DEVICE USING A POLYNOMIAL APPROACH, and U.S. Pat. No. 8,483,843, SENSING VECTOR SELECTION IN A CARDIAC STIMULUS DEVICE WITH POSTURAL ASSESSMENT, and/or US PG Patent Application Pub. Nos. 20170112399, 20170113040, 20170113050, and 20170113053, the disclosures of which are incorporated herein by reference.

In addition, one or more of the ring or tip electrodes 1086A, 1086B, 1086C may be used for therapy delivery. In an example, defibrillation therapy may use coils 1088A, 1088B coupled in common as the opposing pole to the canister 1080, while pacing therapy may use coils 1088A and 1086B as opposing electrodes for post-shock pacing therapy, with a still different combination of electrodes used to provide ventricular pacing therapy for example by pacing between coil 1088B and tip electrode 1086C. In some embodiments, the coil electrode 1078 positioned in the intercostal vein 1064 may also be used as an opposing electrode for post-shock packing therapy or ventricular pacing therapy.

The lead 1080 may be placed as shown such that the proximal coil 1088A is about level with the atria, and distal coil 1088B is about level with the ventricles, if desired. In some examples fewer or different electrodes may be provided on the lead 1080 such as by excluding one or the other of the proximal coil 1088A or distal coil 1088B. Various designs are also shown herein. In some examples, one or more electrodes on the lead 1080 are provided at or inferior to the apex of the heart 1052, or at or superior to the top of the heart 1052.

As described above, placing electrodes in the ITV 1050 as well as an intercostal vein 1064 provides lateral and posterior defibrillation vectors which may reduce defibrillation thresholds. Accessing the intercostal vein 1064 through the brachiocephalic access system described above with respect to FIGS. 4 and 5 and FIGS. 21-25 may allow for the placement of a combination internal thoracic vein lead and an intercostal vein lead (offering an anterior to lateral/posterior defibrillation vector) through a single access point and a left pectoral canister 1080 placement (although other canister locations can be used).

Figure 26:
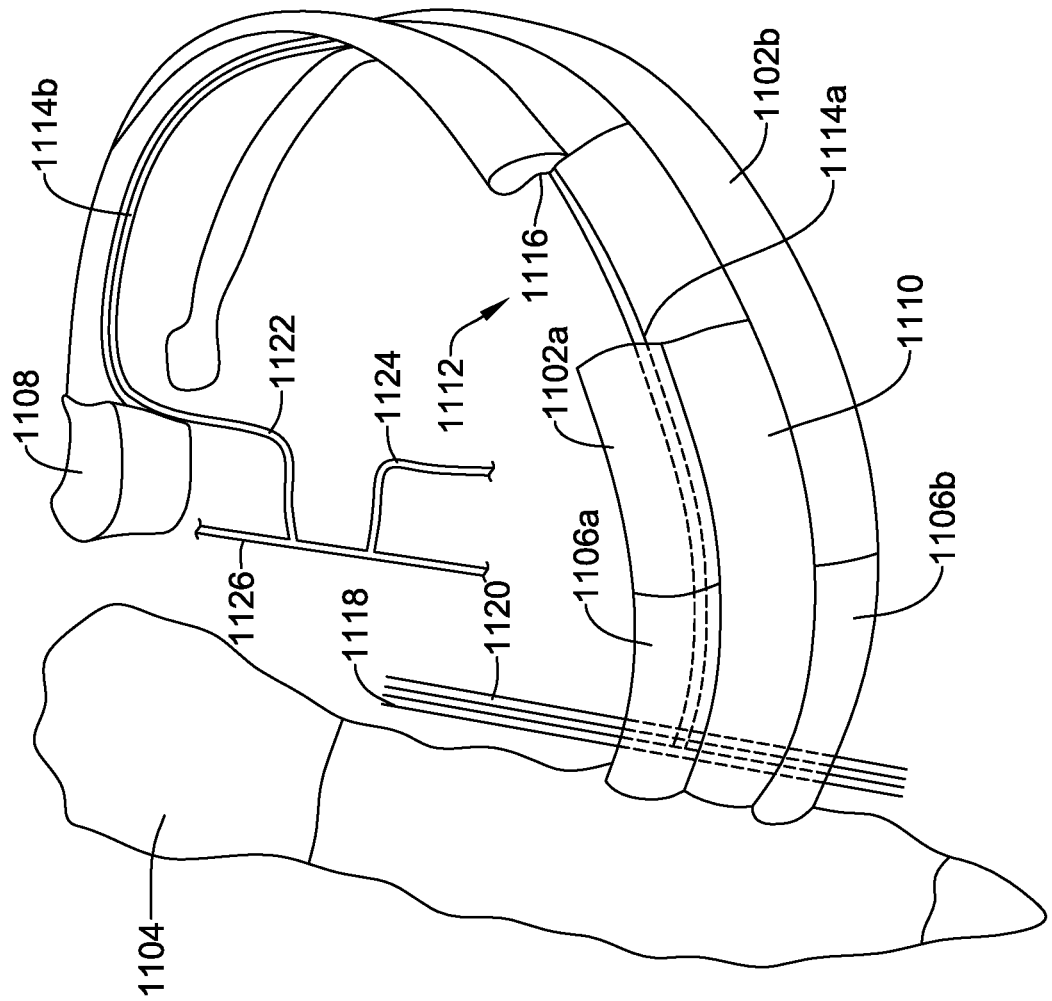
FIGS. 26-31 illustrate another method of implanting a lead in an intercostal vein and the ITV.

In some embodiments, one or more leads can be implanted in the intercostal vein, azygos vein system and/or internal thoracic vein through percutaneous access of an intercostal vein. FIG. 26 illustrates an alternative view of some of the left thoracic anatomy. The ribs 1102a, 1102b (collectively, 1102) are connected anteriorly to the sternum 1104 through costal cartilage 1106a, 1106b (collectively, 1106) and are coupled posteriorly to the spine 1108. It should be understood that, for clarity, not all of the ribs 1102 or other anatomy are illustrated. Intercostal muscle 1110 extends between the ribs 1102. A region of one of the ribs 1102a, and a portion of the intercostal muscle 1110 has been removed at the area generally indicated by arrow 1112 to expose the anterior intercostal vein 1114a disposed in or adjacent to the costal groove 1116 (for clarity, the anterior intercostal artery and the anterior intercostal nerve are not shown). Each rib in the ribcage includes an intercostal vein, artery, and nerve.

The anterior intercostal vein 1114a follows the rib 1102a laterally and posteriorly to become the posterior intercostal vein 1114b. The left anterior intercostal veins 1114a drain to the left ITV 1118, shown next to the internal thoracic artery 1120. The anterior intercostal vein 1114a is shown in phantom under the rib 1102a to further illustrate this connection between the ITV 1118 and the anterior intercostal vein 1114a. While not explicitly shown, the right anterior intercostal veins drain to the right ITV. The posterior intercostal veins 1114b drain to the azygos vein system. The superior left posterior intercostal veins drain to the accessory hemiazygos vein 1122, the inferior left posterior intercostal veins drain to the hemiazygos vein 1124 and the right posterior intercostal veins drain to the azygos vein 1126.

The intercostal vein 1114a, 1114b may be accessed through an intercostal approach. As described above, FIG. 6B illustrates some intercostal access locations usable for superior or inferior access. These access locations are not intended to be limiting. For example, some suitable access points may be laterally and posteriorly displaced from those shown in FIG. 6.

FIGS. 27-31 illustrate the placement of one or more leads in the intercostal vein, azygos vein system and/or internal thoracic vein through percutaneous access of an intercostal vein 1114. For simplicity, the relevant vasculature is shown in isolation. In some cases, it may be desirable to access the intercostal vein in as lateral of a positioned as possible. The intercostal vein 1114 may be blocked from percutaneous blind access by the ridge of the rib (not explicitly shown). In some instances, a blind access approach may be used while in other instances, a cut down procedure may be used to access the intercostal vein 1114. In either approach, the access method may resemble the Seldinger technique, though in this case the muscle in the intercostal space would first be traversed. A needle (not explicitly shown) may be used to establish puncture 1128 using ultrasound guidance, with a guidewire 1130 passed therethrough. Once the puncture 1128 is made and the guidewire 1130 is in the desired blood vessel, the needle is removed, keeping the guidewire 1130 in place, and an appropriately sized introducer sheath 1132 (optionally including a dilator) is placed over the guidewire 1130.

The distal end 1136 of the introducer sheath 1132 may be directed posteriorly towards the posterior intercostal vein 1114b. However, in some cases, the distal end 1136 of the introducer sheath may be directed anteriorly towards the anterior intercostal vein 1114a. A guide catheter 1134 and guidewire 1130 are then introduced through the introducer sheath 1132. The guidewire 1130 may be the same as used in gaining initial access 1128 (if one is used to gain access 1128), or may be a different guidewire. In an example, the guidewire 1130 is preloaded in the guide catheter and both are introduced at the same time until the guide catheter 1134 is at a desired location relative to the ostium of the selected ITV. The guidewire 1130, which may be deflectable or steerable, can then be used to enter the left posterior intercostal vein 1114b. The guide catheter 1134 can then traverse over the guidewire and through the ostium and into the left posterior intercostal vein 1114b. While the procedure is described with respect the left intercostal vein, the same or a similar procedure may be performed using the right intercostal vein.

In some examples, the guide catheter 1134 is introduced first and the guidewire 1130 is introduced next. For example, a steerable or curved guide catheter 1134 may traverse the introducer sheath 1132 to its distal end 1136 and then, using steering of the guide catheter or a precurved structure of the guide catheter, would then turn as shown at 182 to enter the left ITV 158. The guidewire 1130 may be introduced through the guide catheter 1134. In another example, a guidewire 1130 may be omitted.

Figure 27:
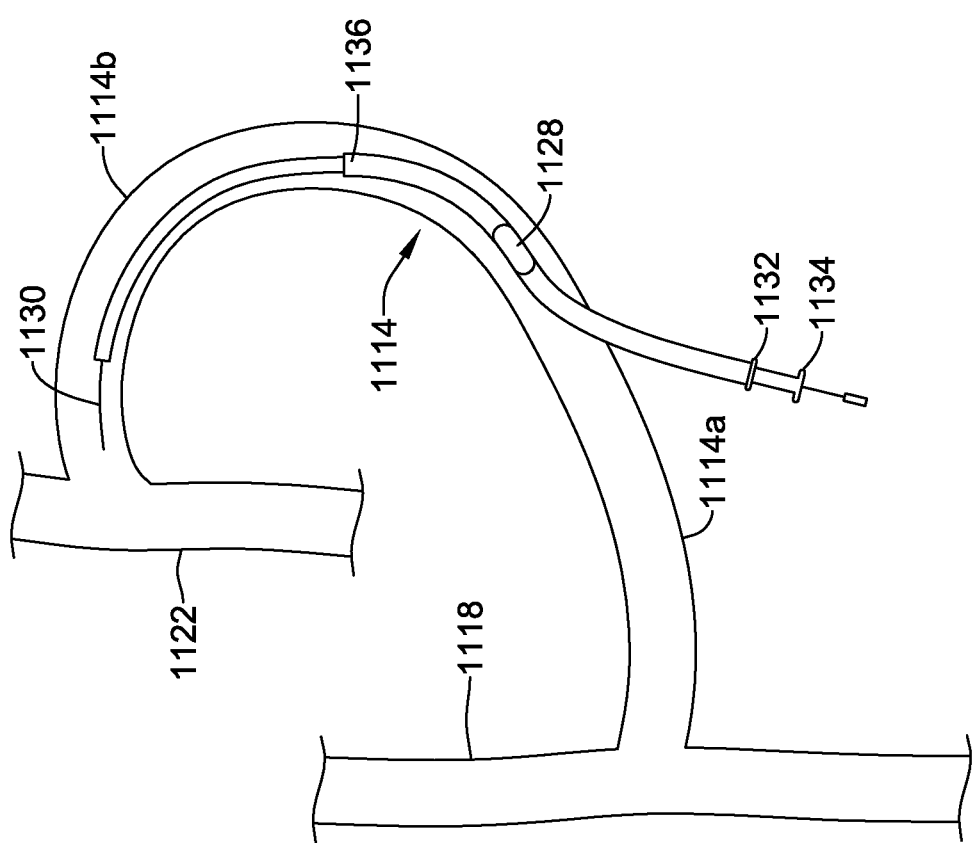
Figure 28:
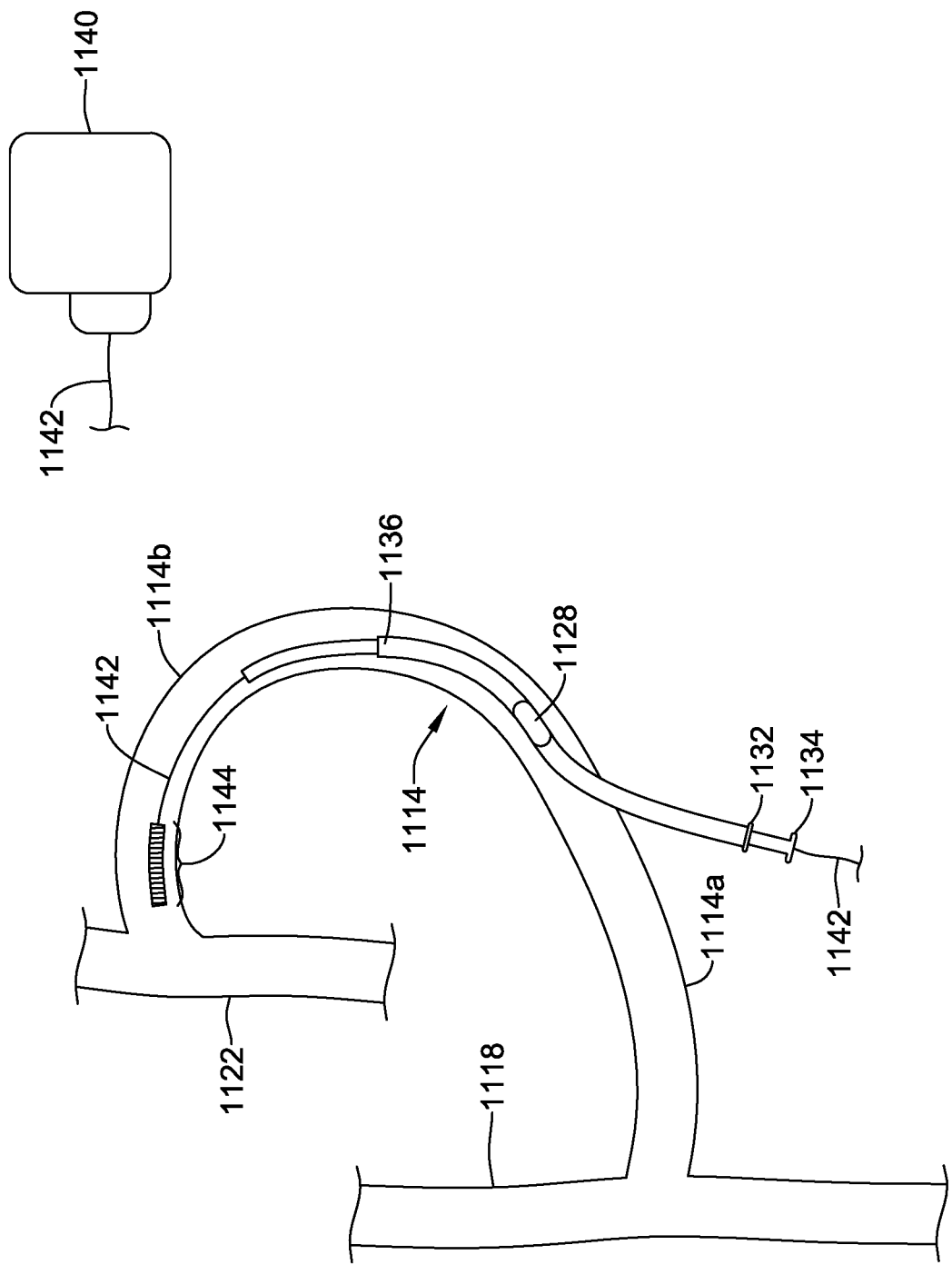

FIG. 28 shows implantation of an implantable cardiac stimulus system. The system includes an implantable pulse generator 1140, similar in form and function to those described herein, which may be placed in the subclavicular location shown (or any other suitable position, as desired). A first lead 1142 passes into the venous access point 1128 into the intercostal vein 1114 and to the posterior intercostal vein 1114b. For such an introduction, in one example, the guide catheter 1134 can be used to direct the lead 1142 through the chosen intercostal vein 1114, with or without use of a guidewire 1130 (FIG. 27).

In some examples, a flexible lead is used having a lumen therein to receive a guidewire or stylet to enhance pushability. In another example, a flexible lead may be introduced with the support of the guide catheter 1134 during advancement. In this latter example, the guide catheter 1134 may receive the lead 1142 through a guide catheter lumen that serves to retain a fixation apparatus or shape for the flexible lead, such as a 2-dimensional or 3-dimensional curvature (see FIGS. 10-11), tines (see FIG. 12), an expandable member (see FIG. 15), or hooks or a side-extending engagement structure (see FIG. 16).

In another alternative, the guide catheter 1134 and guidewire 1130 may be omitted by providing a lead with a flexible or steerable structure, and/or a lead configured for implantation using a steerable stylet. For example, a lead may be configured to be implanted using a steerable stylet in a lumen thereof, possibly using contrast visualization, if desired. Once initial access is achieved, simply pushing the stylet should be sufficient to implant the lead to a desired level in the intercostal vein 1114. The stylet may have a secondary function of preventing an anchoring structure of the lead from assuming an anchoring shape or releasing an anchoring tine, hook, expandable member, stent or other device.

In the example, the lead 1142 includes a coil electrode as shown at 1144. The coil electrode 1144 may include a high voltage coil that may also serve as a pacing anode. However, any of the lead designs described with respect to FIGS. 5 and 10-19 may be used. Further, while an anchoring mechanism is not explicitly shown, the lead can be fixated in the vasculature using various means such as tines, hooks, biases, T-bar tethers, and other means. The proximal end of the lead 1142 may be connected to an implantable pulse generator 1140. While the coil electrode 1144 is illustrated as being positioned in the posterior intercostal vein 1114b, the electrode 1144 may be positioned in the accessory hemiazygos vein 1122 and/or the hemiazygos vein 1124 (or the azygos vein 1126, if access is from the right), as desired. In order to access the azygos vein system, a telescoping catheter system may be used. For example, an inner and outer catheter system, such as that described with respect to FIGS. 21-25 may be used.

Figure 29:
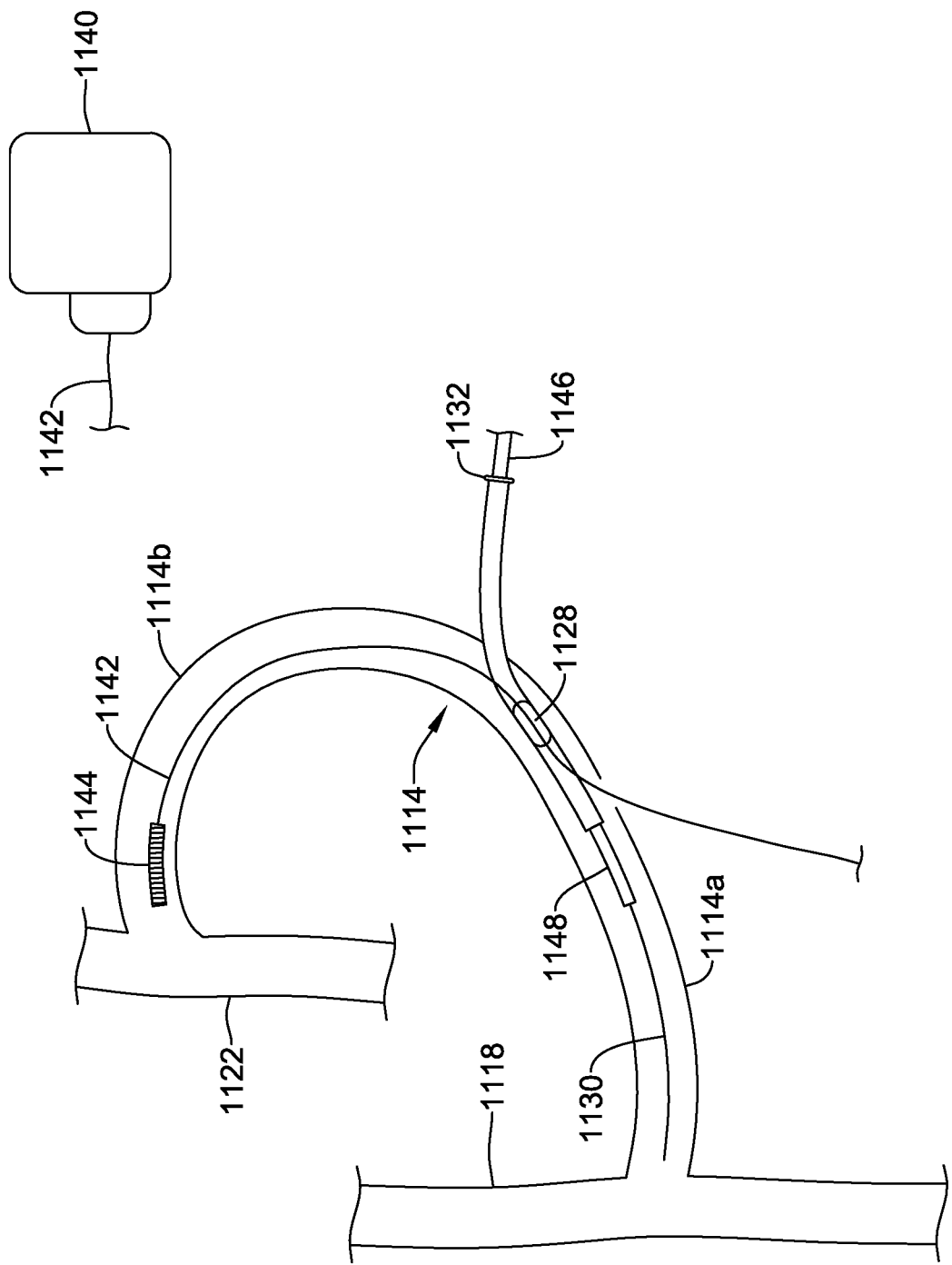
Figure 30:
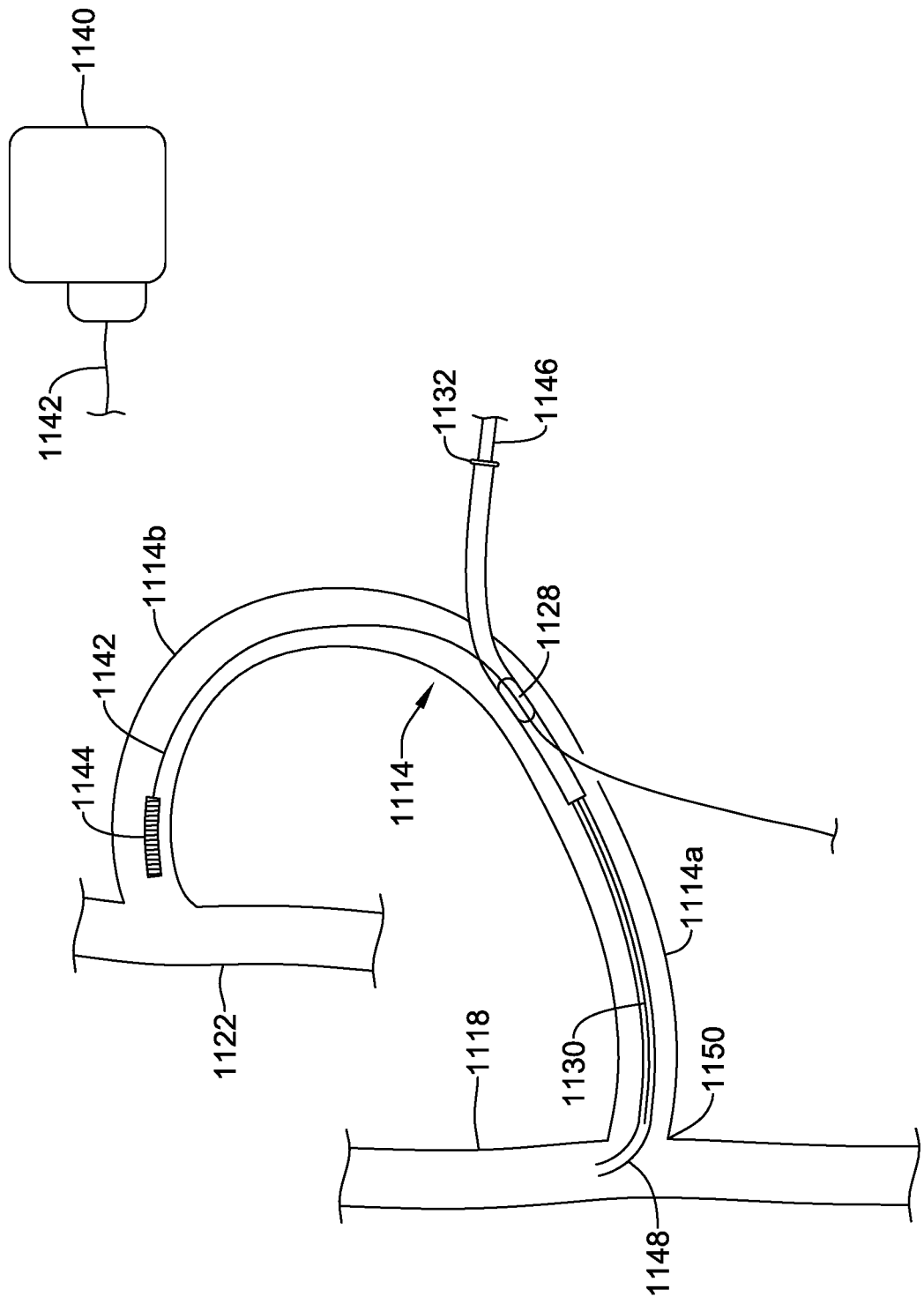

After placement of the first lead 1142, the introducer sheath 1132 may be removed. It is contemplated that during placement of the first lead 1142, the guidewire 1130 may be retained. After removal of the introducer sheath 1132, the guidewire 1130 may be oriented within the same intercostal vein 1114 in the anterior direction, as shown in FIG. 29. The introducer sheath 1132 may be placed over the guidewire 1130. The introducer sheath 1132 may be the same or different from the introducer sheath used to place the first lead 1142. A catheter 1146 may be advanced through the introducer sheath 1132 and towards the ITV 1118. The catheter 1146 may be similar in form and function to the inner catheter 1060 described herein. For example the catheter 1146 may include a curved distal end region 1148 to facilitate navigation through the vasculature. In some instances, the curved distal end region 1148 may have a curve of 90° or greater. Although, the curve can be less than 90°, as desired. In other instances, the distal end region 1148 may be deflectable (e.g., through pull wires or other deflection mechanism) to allow the user to deflect (e.g., bend) the catheter 1146 as needed. In some cases, the guidewire 1130 may be sufficiently rigid to maintain the distal end region 1148 in a substantially straight configuration. The catheter 1146 may be advanced distally beyond the distal end of the guidewire 1130 such that the distal end region 1148 can assume its predefined curved configuration, or be deflected into a curved configuration, as shown in FIG. 30. The curved distal end region 1148 may be used to identify the opening the junction 1150 between an intercostal vein 1114 and the ITV 1118.

Figure 31:
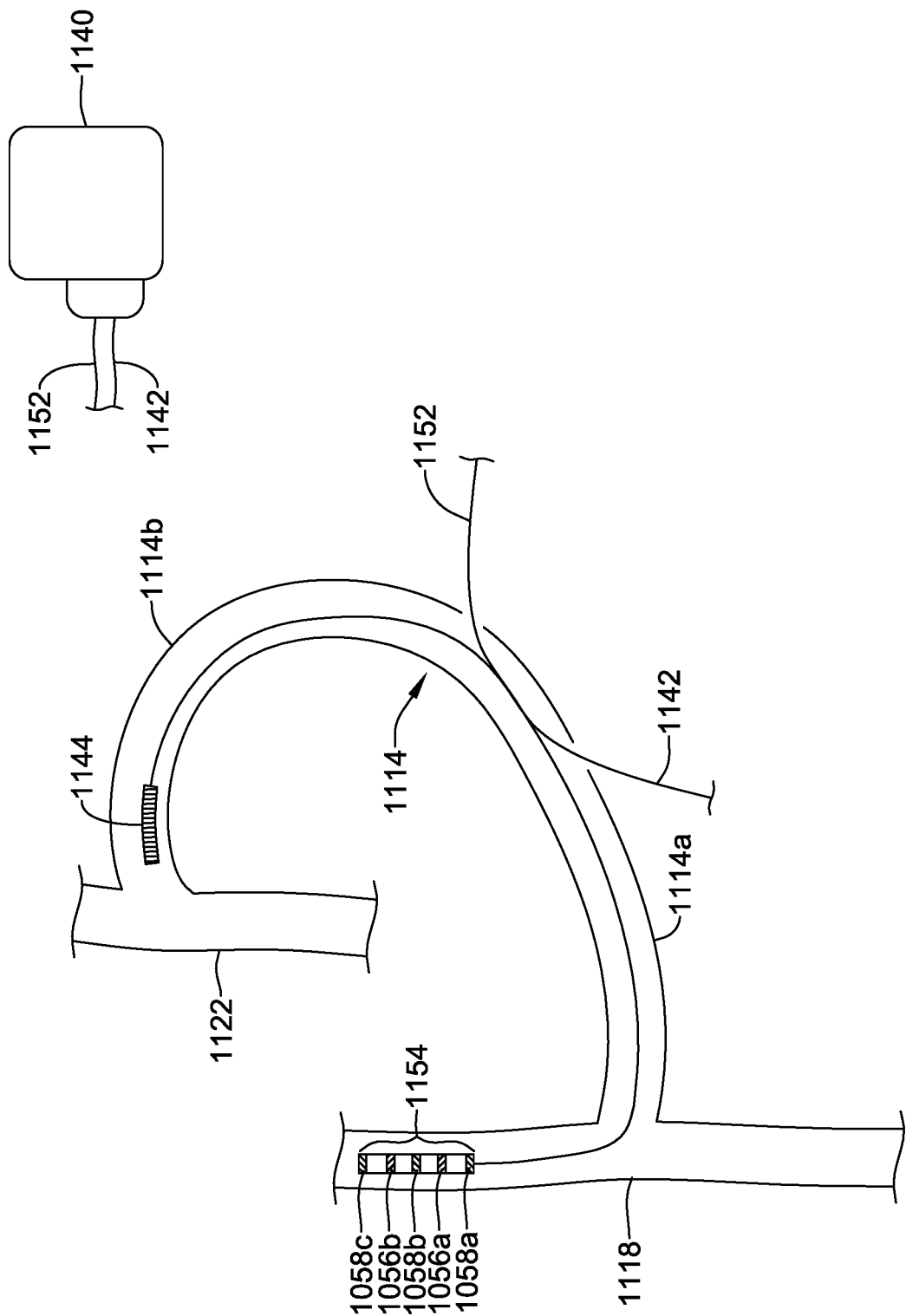

A second lead 1152 may be advanced through the catheter 1146 and into the ITV 1118, as shown in FIG. 31. The lead 1152 may be advanced in a similar manner to any of the leads described herein. The guidewire 1130 and the catheter 1146 and/or introducer sheath 1132 (if still in the vessel) may be removed after placement of the lead 1152.

In the example, the second lead 1152 includes a multi-electrode distal structure as shown at 1154. However, any of the lead designs described with respect to FIGS. 5 and 10-19 may be used. Further, while an anchoring mechanism is not explicitly shown, the lead can be fixated in the mediastinum using various means such as tines, hooks, biases, T-bar tethers, and other means. In addition to the engaging members described herein some illustrative additional anchoring mechanisms are discussed in US PG Patent Application Pub. No. 20170021159, titled SUBSTERNAL PLACEMENT OF A PACING AND/OR DEFIBRILLATING ELECTRODE, as well as US PG Patent Application Pub. No. 20170095657, titled FIXATION DEVICE FOR A SUBCUTANEOUS ELECTRODE, the disclosures of which are incorporated herein by reference. In some cases, the leads 1142, 1152 may be combined into or connected to a single wire for connection to the pulse generator 1140, although this is not required.

In some cases, the lead 1152 may be placed on the left side of the patient. In other examples, the right side of the patient may instead or in addition to be accessed, including the right ITV. Access to the right ITV may be achieved by advancing a guide catheter and/or guidewire from in any of the manners described herein.

In some examples, a lead 1152 may be placed in both the left and right ITVs. In such an instance, a lead 1152 is delivered through each of the left and right ITV in a manner similar to that described with respect to FIGS. 29-31. Pacing between right and left side lead placements may be performed to target specific chambers or chamber combinations, or sensing may be performed using one pair of electrodes with therapy delivery using a different pair of electrodes to achieve resynchronization or other desirable effect.

In this example, the lead structure includes a proximal coil 1156A separate from a distal coil 1156B. The coils 1156A/B and canister 1140 may serve as therapy delivery electrodes. As such there may be multiple therapy vectors such as between coil 1156A and coil 1156B, between either of coils 1156A and 1156B and the canister 1140, or between a combination of two of the three therapy electrodes 1156A, 1156B and canister 1140, and the third such electrode, such as by linking coils 1156A and 1156B in common as the anode or cathode relative to the canister 1140. Alternatively, or additionally vectors may be between either of coils 1156A and 1156B and the coil electrode 1144 in the intercostal vein 1114.

A plurality of ring electrodes may be provided as shown at 1158A, 1158B, and 1158C. Electrode 1158C may also or instead be a tip electrode. Electrodes 1158A/B/C may serve as sensing electrodes. The coils 1156A, 1156B may also serve as sensing electrodes. These various electrodes may be used for sensing cardiac signals in various combinations using, for example, methods and circuitry discussed in U.S. Pat. No. 7,783,340, titled SYSTEMS AND METHODS FOR SENSING VECTOR SELECTION IN AN IMPLANTABLE MEDICAL DEVICE USING A POLYNOMIAL APPROACH, and U.S. Pat. No. 8,483,843, SENSING VECTOR SELECTION IN A CARDIAC STIMULUS DEVICE WITH POSTURAL ASSESSMENT, and/or US PG Patent Application Pub. Nos. 20170112399, 20170113040, 20170113050, and 20170113053, the disclosures of which are incorporated herein by reference.

In addition, one or more of the ring or tip electrodes 1158A, 1158B, 1158C may be used for therapy delivery. In an example, defibrillation therapy may use coils 1156A, 1156B coupled in common as the opposing pole to the canister 1140, while pacing therapy may use coils 1156A and 1158B as opposing electrodes for post-shock pacing therapy, with a still different combination of electrodes used to provide ventricular pacing therapy for example by pacing between coil 1156B and tip electrode 1158C. In some embodiments, the coil electrode 1144 positioned in the intercostal vein 1114 may also be used as an opposing electrode for post-shock packing therapy or ventricular pacing therapy.

The lead 1140 may be placed as shown such that the proximal coil 1156A is about level with the atria, and distal coil 1156B is about level with the ventricles, if desired. In some examples fewer or different electrodes may be provided on the lead 1140 such as by excluding one or the other of the proximal coil 1156A or distal coil 1156B. Various designs are also shown herein. In some examples, one or more electrodes on the lead 1140 are provided at or inferior to the apex of the heart, or at or superior to the top of the heart.

As described above, placing electrodes in the ITV 1118 as well as an intercostal vein 1114 provides lateral and posterior defibrillation vectors which may reduce defibrillation thresholds. Accessing the intercostal vein 1114 through the intercostal space as described herein may allow for the placement of a combination internal thoracic vein lead and an intercostal vein lead (offering an anterior to lateral/posterior defibrillation vector) through a single access point and a left pectoral canister 1140 placement (although other canister locations can be used).

Figure 32:
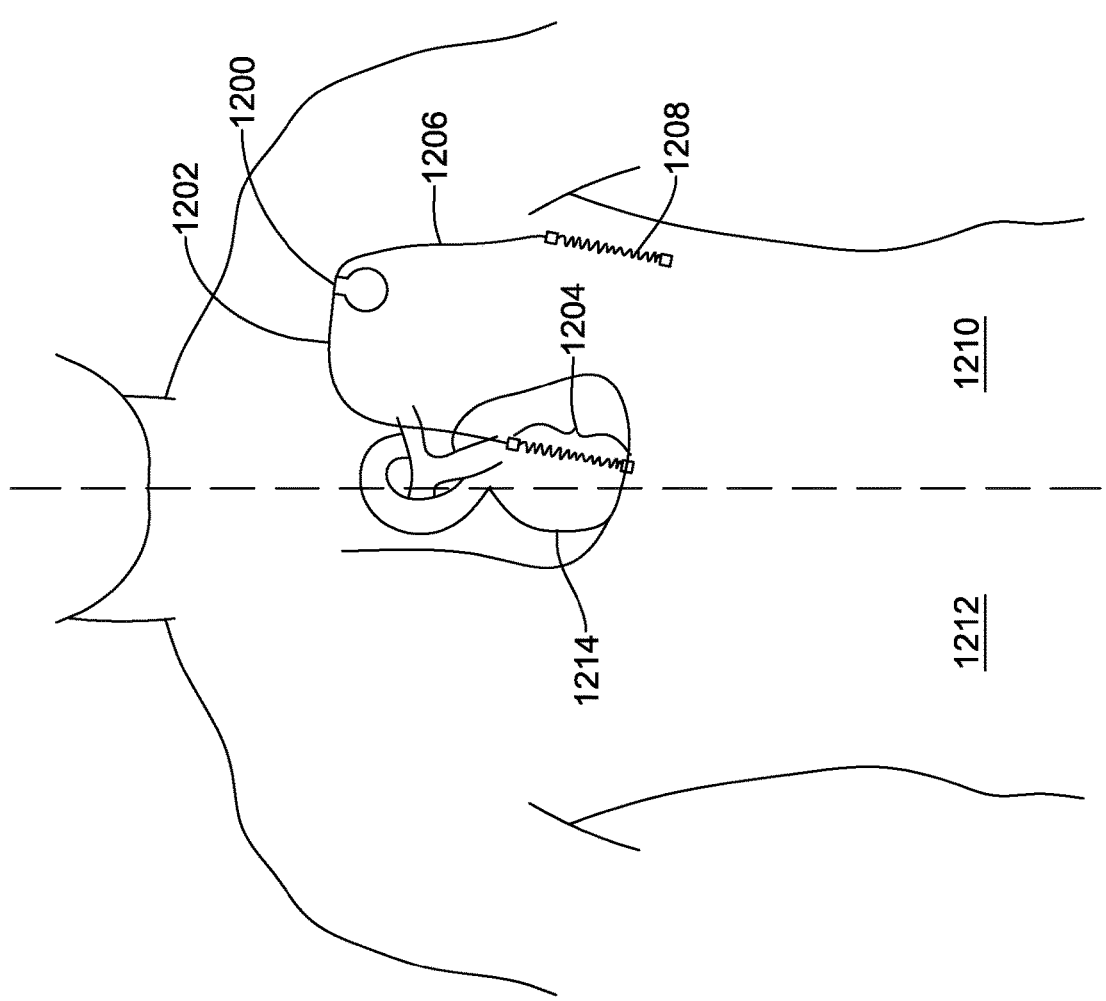
FIGS. 32-33 show illustrative implant locations for a first electrode and a second electrode.

Alternative arrangements for anterior and posterior lead placements are also contemplated. FIG. 32 illustrates an example alternative arrangement of an implantable cardiac stimulus system. The system includes an implantable pulse generator 1200 which may be placed in the left subclavicular or pectoral location shown (or any other suitable position, as desired). A lead 1202 is passed into the left internal thoracic vein using any of the methods described herein such that an electrode 1204 is positioned relatively near to the heart 1214 such as by being placed level with the heart 1214 within the left ITV.

From the pectoral device pocket, a second lead 1206 may be tunneled such that an electrode 1208 subcutaneously near or substantially near the left axilla. A tunneling tool may be used as shown, for example, in U.S. Pat. No. 8,157,813, titled APPARATUS AND METHOD FOR SUBCUTANEOUS ELECTRODE INSERTION, and/or U.S. Pat. No. 8,718,793, titled ELECTRODE INSERTION TOOLS, LEAD ASSEMBLIES, KITS AND METHODS FOR PLACEMENT OF CARDIAC DEVICE ELECTRODES, the disclosures of which are incorporated herein by reference, or using any other suitable tunneling tools and methods.

Tunneling in this manner may position the electrode laterally and posteriorly from the first electrode 1204. It is contemplated that the second electrode 1208 may be positioned near the anterior axillary line, the mid axillary line, or the posterior axillary line. In some cases, the second lead 1206 may be tunneled such that the electrode 1208 is disposed subcutaneously in an even further posterior position, such as, but not limited to, near the patient's back and/or posterior ribs. It is contemplated that the second electrode 1208 may be positioned in any number of configurations, as desired. In one example, the electrode 1208 could be tunneled towards the midaxillary line and then turned to terminate anteriorly. As described above, placing electrodes 1204, 1208 in the ITV as well as in a position laterally and posteriorly displaced therefrom provides lateral and posterior defibrillation vectors which may reduce defibrillation thresholds. The pulse generator 1200 may or may not serve as an electrode along with the first electrode 1204 and the second electrode 1208.

The electrodes 1204, 1208 may be multiple array type electrodes or single coil electrodes, as desired. The electrodes 1204, 1208 may have a coil length in the range of 8 centimeters (cm) to greater than 25 cm. The length of the coil may be determined, at least in part, by the implant location. For example, the second electrode 1208 may be a longer coil (e.g., longer than the first electrode 1204) placed to cover a substantial portion of the left axilla and then proceed towards the anterior or posterior chest, as desired. In some cases, the electrodes 1204, 1208 may include patches, disks, and/or deployable electrodes to increase the surface area of the electrode. In some cases, alternative electrode structures may require additional incisions to place a larger electrode.

The illustration shown in FIG. 32 places the lead on the left side 1210 of the patient. In other examples, the right side 1212 of the patient may instead or in addition be accessed, including the right ITV. Access to the right ITV may be achieved using any of the methods described herein.

In another example, both the left and right ITVs could be utilized to enable a multi-chamber pacing and/or sensing system. Alternatively or additionally, electrodes could be placed in both the left and right ITVs as well one or both of the left or right axilla. Such systems may work in a complementary fashion with other devices including, but not limited to leadless pacemakers and/or event monitors. It is further contemplated that such systems may also provide energy to power various leadless systems placed in the heart 1214 or elsewhere.

Figure 33:
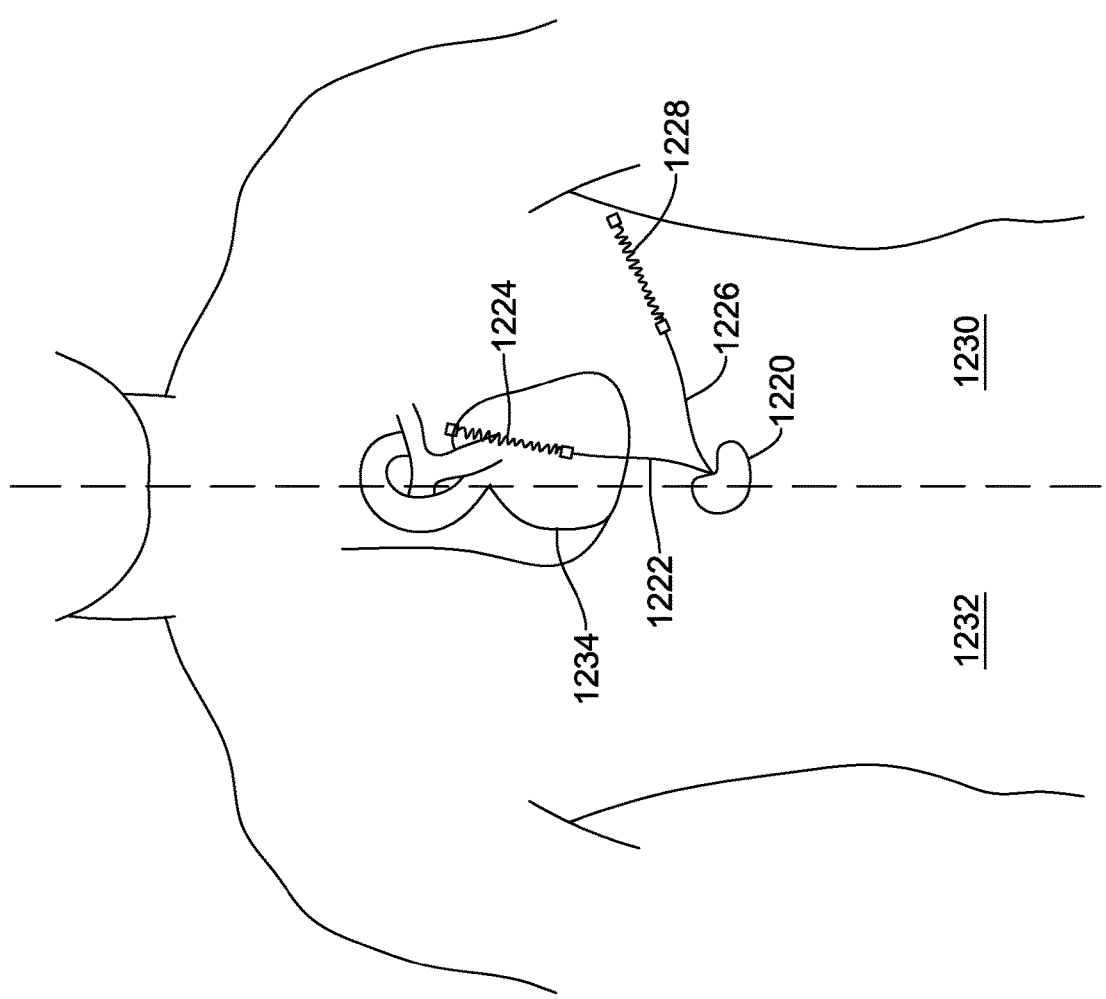
Figure 34:
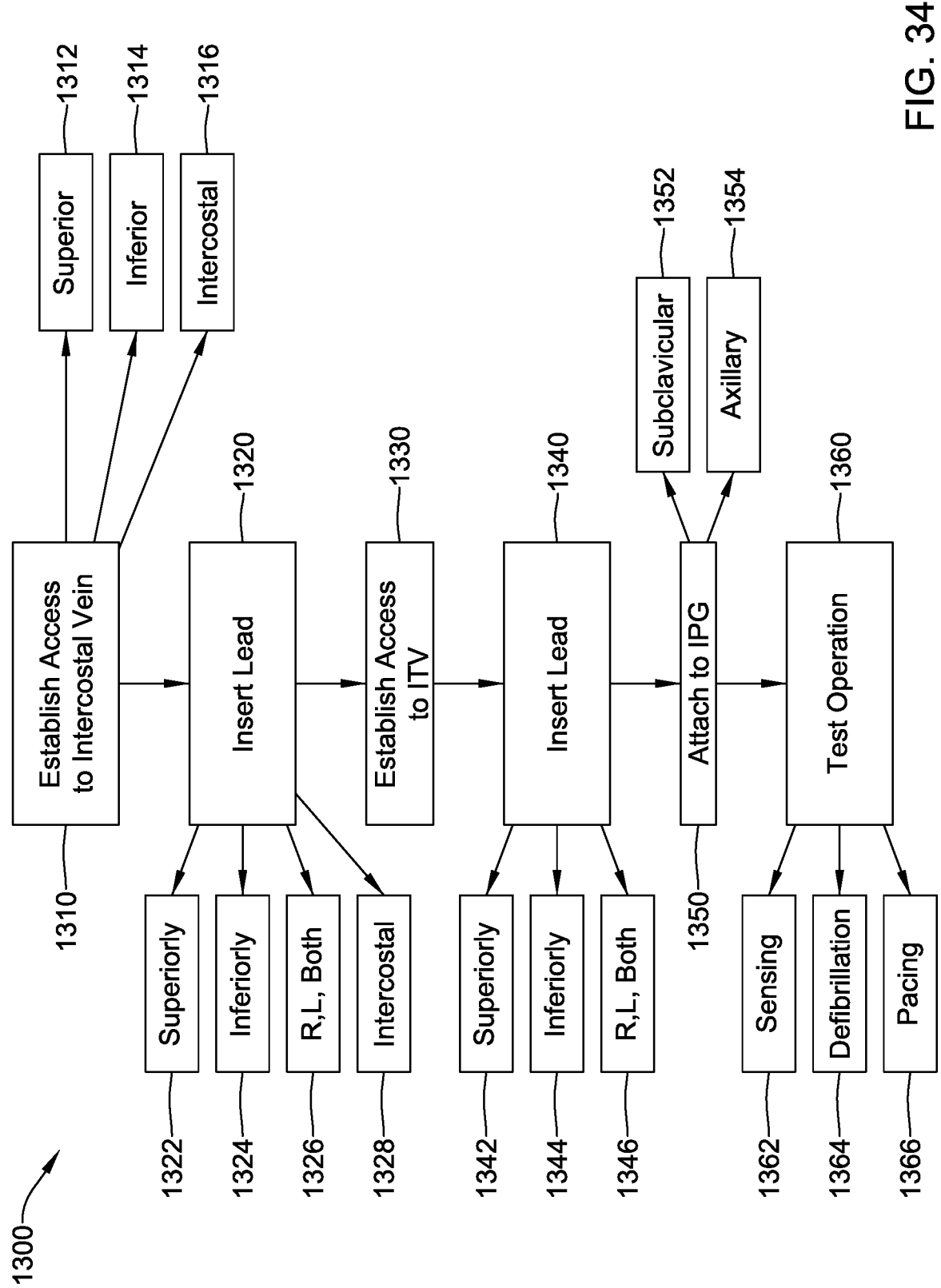
FIG. 34 is a block flow diagram for an illustrative method.

FIG. 33 illustrates an example of another alternative arrangement of an implantable cardiac stimulus system. The system includes an implantable pulse generator 1220 which may be placed in or near the paraxiphoid window or left axillary (or any other suitable position, as desired). A lead 1222 is passed into the left internal thoracic vein through a selected superior epigastric vein or musculophrenic vein using any of the methods described herein such that an electrode 1224 is positioned at a desired location such as near to the heart 1234 within the left or right ITV.

From the device pocket, a second lead 1226 may be tunneled such that an electrode 1228 subcutaneously near or substantially near the left axilla. This may position the electrode laterally and posteriorly from the first electrode 1224. It is contemplated that the second electrode 1228 may be positioned near the anterior axillary line, the mid axillary line, or the posterior axillary line. In some cases, the second lead 1226 may be tunneled such that the electrode 1228 is disposed subcutaneously in an even further posterior position, such as, but not limited to, near the patient's back and/or posterior ribs. As described above, placing electrodes 1224, 1228 in the ITV as well as in a position laterally and posteriorly displaced therefrom provides lateral and posterior defibrillation vectors which may reduce defibrillation thresholds. The pulse generator 1220 may or may not serve as an electrode along with the first electrode 1224 and the second electrode 1228.

The electrodes 1224, 1228 may be multiple array type electrodes or single coil electrodes, as desired. The electrodes 1224, 1228 may have a coil length in the range of 8 cm to greater than 25 cm. The length of the coil may be determined, at least in part, by the implant location. For example, the second electrode 1228 may be a longer coil (e.g., longer than the first electrode 1224) placed to cover a substantial portion of the left axilla and then proceed towards the anterior or posterior chest, as desired. In some cases, the electrodes 1224, 1228 may include patches, disks, and/or deployable electrodes to increase the surface area of the electrode. In some cases, alternative electrode structures may require additional incisions to place a larger electrode.

The illustration shown in FIG. 33 places the lead on the left side 1230 of the patient. In other examples, the right side 1232 of the patient may instead or in addition be accessed, including the right ITV. Access to the right ITV may be achieved using any of the methods described herein.

In another example, both the left and right ITVs could be utilized to enable a multi-chamber pacing and/or sensing system. Alternatively or additionally, electrodes could be placed in both the left and right ITVs as well one or both of the left or right axilla. Such systems may work in a complementary fashion with other devices including, but not limited to leadless pacemakers and/or event monitors. It is further contemplated that such systems may also provide energy to power various leadless systems placed in the heart 1234 or elsewhere.

FIG. 30 is a block flow diagram for an illustrative method for providing a cardiac stimulus system to a patient. As shown at 1300, the method comprises establishing access to the intercostal vein 1310, inserting a lead in the intercostal vein 1320, establishing access to the ITV 1330, inserting a lead in the ITV 1340, attaching an IPG to the lead(s) 1350, and performing test operations 1360.

For example, establishing access to the intercostal vein 1310 may include accessing from a superior position 1312 such as by entering the subclavian vein and passing through the ostium of the ITV in the brachiocephalic vein and then entering the intercostal vein from the ITV. In another example, establishing access to the intercostal vein 1310 may include accessing from an inferior position 1314 such as by entering the superior epigastric vein and passing superiorly therefrom into the ITV and then entering the intercostal vein from the ITV. In some examples, access via locations 1312, and 1314 may include accessing via a second blood vessel such as by accessing superiorly 1312 by way of the subclavicular vein and brachiocephalic vein, or accessing inferiorly 1314 through the superior epigastric vein. In still another example, establishing access to the intercostal vein 1310 may include accessing in an intercostal space 1316 such as by penetrating an intercostal space and entering the ITV using a Seldinger technique.

In an example, inserting a lead 1320 into the intercostal vein may include insertion superiorly 1322, such as by starting in an inferior position 1312 inferior to the lower rib margin and advancing the lead in a superior direction. For another example, inserting a lead 1320 may include insertion inferiorly 1324 that is, starting at a superior location 1314 or at a superior intercostal location 1316, and advancing the lead in an inferior direction. In either such example, the right ITV, left ITV, or both ITV vessels may be used to place a lead in the intercostal vein, as indicated at 1336. Alternatively, the intercostal vein may accessed directly 1328 via the intercostal space 1316.

Establishing access to the ITV 1330 may include accessing from a superior position 1312 such as by entering the subclavian vein and passing through the ostium of the ITV in the brachiocephalic vein. In another example, establishing access to the ITV 1330 may include accessing from an inferior position 1314 such as by entering the superior epigastric vein and passing superiorly therefrom into the ITV. In some examples, access via locations 1312, and 1314 may include accessing via a second blood vessel such as by accessing superiorly 1312 by way of the subclavicular vein and brachiocephalic vein, or accessing inferiorly 1314 through the superior epigastric vein. In still another example, establishing access to the intercostal vein 1310 may include accessing in an intercostal space 1316 such as by penetrating an intercostal space and entering the ITV using a Seldinger technique.

In an example, inserting a lead in the ITV 1340 may include insertion superiorly 1342, such as by starting in an inferior position 1312 inferior to the lower rib margin or intercostally 1316 from an inferior intercostal location (e.g., via an intercostal vein), and advancing the lead in a superior direction. For another example, inserting a lead 1340 may include insertion inferiorly 1344, that is starting at a superior location 1314 or at a superior intercostal location 1316 (e.g., via an intercostal vein), and advancing the lead in an inferior direction. In either such example, the right ITV, left ITV, or both ITV vessels may be used to place a lead in the mediastinum, as indicated at 1346.

During the implantation procedures, contrast or other visualization may be used in various ways. For example, when using a superior access 1312 to the ITV, entering for example via the brachiocephalic vein, contrast or other visualization may be used to track the position of a guidewire, guide catheter or the lead itself into the ostium and then down in to the ITV. In addition, regardless the access route to the ITV, the step of establishing access to the mediastinum may include use of visualization to observe the exit from the ITV and into the mediastinum. Lateral X-ray or other visualization may be used as well to observe lead positioning both in terms of how superior/inferior the lead and its electrodes are, as well as whether the lead is deep enough or shallow enough, as the case may be, in the mediastinum to achieve therapy and/or anchoring aims, and to avoid piercing or poking the lung and/or pericardium, if desired.

Other vessels and implanted lead locations may also be used (such as having a lead in the right ITV, left ITV, both ITVs, azygos vein, an intracardiac lead, a subcutaneous lead) or additional devices such as a separately implanted leadless cardiac pacemaker may be included as well. In a further example, one or more of the transverse veins that flow into the ITV may be used for placement of an electrode or lead. For example, upon accessing an ITV, a physician may further access and emplace a lead or electrode into one of the anterior intercostal veins which run along the intercostal spaces of the anterior chest.

In an example, attaching to an IPG may include attaching to a canister 1350 located in a subclavicular location 1352, historically a common place to put an implanted canister for a transvenous defibrillator or pacemaker. In another example, attaching to an IPG may include attaching to a canister located in an axillary position 1354, such as that used with the S-ICD System. Other IPG locations may be used. Attachment may be directly to the IPG or to a splitter, yoke, or lead extension, if desired.

In an example, test operation 1360 may be used to verify one or both of device functionality and efficacy. For example, sensing operations 1362 may be tested and configured to check for adequate signal availability, for example, or by setting gain, filtering, or sensing vector selection parameters. Defibrillation operations 1364 may be tested by inducting an arrhythmia such as a ventricular fibrillation to determine whether the device will sense the arrhythmia and, if the arrhythmia is sensed, to ensure that the device can adequately provide therapy output by delivering defibrillation at a preset energy. Defibrillation testing 1364 may include determining for a given patient an appropriate defibrillation threshold, and setting a parameter for therapy delivery at some safety margin above the defibrillation threshold.

Prior transvenous systems would typically deliver up to 35 Joules of energy at most, with storage of up to 40 Joules of energy, using peak voltages in the range of up to nearly 1300 volts. The S-ICD System can deliver up to 80 Joules of energy, with 65 Joules often used for in-clinic system testing, with a peak voltage in the range of 1500 volts. The ITV location may facilitate energy levels similar to those of traditional transvenous systems (5-35 Joules, approximately), or may be somewhat higher (5 to about 50 joules, for example), or may still be higher (10 to about 60 joules, for example). Pacing thresholds may also be closer to those for traditional transvenous systems than the more recent S-ICD System.

In an example, pacing testing operation 1366 may include determining which, if any, available pacing vectors are effective to provide pacing capture. If desired, parameters may be tested as well to determine and optimize settings for delivery of cardiac resynchronization therapy. This may include testing of pacing thresholds to optimize energy usage and delivery, as well as checking that adverse secondary effects, such as patient sensation of the delivered pacing or inadvertent stimulation of the phrenic nerve, diaphragm or skeletal muscles are avoided.

In some cases, the left and/or right ITV may be used to access the mediastinum. The target location in region generally contains some loose connective tissues, muscle, nerves and blood vessels. Anchoring a lead may be desirable, for example, in the region between the left and/or right ITV (and beneath the rib cage) and a lateral side of the heart. From such a position, beneath the rib cage, the amount of energy required for defibrillation and pacing efficacy would logically be lower than outside of the sternum and/or rib cage, since the mediastinum location is closer to the heart and bone is generally not a very good conductor of electrical energy, at least when speaking in terms of the tissues in the human body. However, tunneling in this region is not as necessary as it may be in other locations, particularly the subcutaneous space, where the innermost layers of dermis must be separated from underlying muscle, connective tissue and fascia. Indeed, the insertion of a lead through the ITV (e.g., using any of superior access, inferior access, and/or intercostal access) may enable safe placement in the mediastinum.

In any of the above examples, additional lead placement may take place. For example, an additional lead may be placed subcutaneously, within the heart, or in a different blood vessel such as the azygos vein. Additional device placement may occur as well, including, for example, the placement of a leadless cardiac pacemaker in one or more chambers of the heart.

The above examples facilitate a number of therapy options. For example, defibrillation therapy may be delivered in various configurations such as, without limitation:

Between a left ITV electrode or combination of electrodes and a right ITV electrode or combination of electrodes;

Between a left ITV electrode and a device housing placed in the left axilla or left subclavicular location;

Between a right ITV electrode and a device housing placed in the left axilla or left subclavicular location;

Between a left ITV electrode and a device housing placed in the right axilla or right subclavicular location;

Between left and right ITV electrodes electrically in common and a right or left axillary or subclavicular canister;

Between one ITV electrode and a second ITV electrode in common with a device canister in the left or right axilla or subclavicular location;

Between a first electrode on a lead, and a second electrode on the same lead, where the first and second electrodes are in the same ITV;

Between a first electrode on a lead, and a second electrode on the same lead, where the first electrode is in an ITV, and the second electrode is in a tunnel leading to access to the ITV, such as in the inframammary crease on lead 410 in FIG. 7;

Between a left ITV electrode or combination of electrodes and a left axilla electrode or combination of electrodes;

Between a right ITV electrode or combination of electrodes and a right axilla electrode or combination of electrodes;

Between a left ITV electrode or combination of electrodes and a right axilla electrode or combination of electrodes;

Between a right ITV electrode or combination of electrodes and a left axilla electrode or combination of electrodes.

In these examples, a "left ITV electrode" or "right ITV electrode" may include a single coil electrode or a combination of plural coils and/or one or more coils with one or more ring electrodes electrically in common. The above combinations may also be used for delivery of a bradycardia pacing therapy or an anti-tachyarrhythmia pacing therapy.

Further examples may provide a resynchronization therapy by delivering pacing pulses in various configurations, such as, without limitation:

In bipolar fashion within the left ITV to pace the left ventricle, and also in bipolar fashion within the right ITV to pace the right ventricle, with relative timing between the two sets of pacing therapies determined according to analysis of cardiac output or electrical response.

In bipolar fashion within one of the left or right ITV to stimulate a respective left or right ventricle in response to atrial sensed signals sensed with electrodes placed in an ITV at a superior location level with the atria.

In monopolar fashion between a device housing and one or both of left or right ITV electrodes, using for timing information atrial signals sensed using additional electrodes in at least one ITV and/or far-field sensed morphology detected using a device housing.

In an example, a heart failure or resynchronization therapy may be delivered as follows, with reference to FIG. 7. A pacing therapy may be delivered by sensing atrial activity using the distal two ring electrodes shown in the electrode assembly 412 to determine timing for pace therapy delivery using the proximal coil electrode and canister 414. Numerous other combinations may be had as can be seen to those skilled in the art.

Some embodiments of the present invention may take the form of an implantation tool set configured for use in implanting a cardiac device, such as a lead, into an ITV. Some such embodiments may include an introducer sheath. Some such embodiments may include a guide catheter. Some such embodiments may include a guidewire. Some such embodiments may further include a tool set for performing a Seldinger technique to access a blood vessel percutaneously.

Some embodiments of the present invention take the form of an implantable cardiac stimulus device comprising a lead and an implantable canister for coupling to the lead, the implantable canister housing operational circuitry configured to deliver output therapy in the form of at least one of bradycardia pacing, anti-tachycardia pacing, cardiac resynchronization therapy, or defibrillation, using a lead implanted in an ITV and a canister implanted in a patient.

As used herein, a coil electrode may be a helically wound element, filament, or strand. The filament forming the coil may have a generally round or a generally flat (e.g. rectangular) cross-sectional shape, as desired. However, other cross-sectional shapes may be used. The coil electrode may have a closed pitch, or in other words, adjacent windings may contact one another. Alternatively, the coil electrode may have an open pitch such that adjacent windings are spaced a distance from one another. The pitch may be uniform or varied along a length of the coil electrode. A varied pitch may be gradual tapered changes in pitch or abrupt or step-wise changes in pitch.

A coil electrode may have a length L that is generally larger than a width W. Round, oval or flattened coil electrodes may be used. Coil electrodes may have a length in the range of one to ten centimeters. In an example, a coil having a six or eight centimeter length may be used. In another example, a lead may have two four centimeter coils. Coils and leads may be in the range of four to ten French, or larger or smaller, in outer profile.

Coils and leads may be coated. For example, a thin permeable membrane may be positioned over a shock coil or other electrode and/or other portions of the lead to inhibit or to promote tissue ingrowth. Coatings, such as, but not limited to expanded polytetrafluoroethylene (ePTFE) may also be applied to the coil and/or lead to facilitate extraction and/or to reduce tissue ingrowth. In some embodiments, one or more of the electrodes, whether coils, rings, or segmented electrodes, include a high capacitive coating such as, but not limited to iridium oxide (IrOx), titanium nitride (TiN), or other "fractal" coatings which may be used, for example, to improve electrical performance. Steroidal and antimicrobial coatings may be provided as well.

The various components of the devices/systems disclosed herein may include a metal, metal alloy, polymer, a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers for use in the leads discussed above may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS A), polycarbonates, ionomers, biocompatible polymers, other suitable materials, or mixtures, combinations, copolymers thereof, polymer/metal composites, and the like.

In at least some embodiments, portions or all of the accessory devices and their related components may be doped with, made of, or otherwise include a radiopaque material. Radiopaque materials are understood to be materials capable of producing a relatively bright image on a fluoroscopy screen or another imaging technique during a medical procedure. This relatively bright image aids the user of the accessory devices and their related components in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the accessory devices and their related components to achieve the same result.

Any guidewire, introducer sheath, and/or guide catheter design suitable for medical interventions may be used for accessing the venous structures discussed herein.

The implantable systems shown above may include an implantable pulse generator (IPG) adapted for use in a cardiac therapy system. The IPG may include a hermetically sealed canister that houses the operational circuitry of the system. The operational circuitry may include various elements such as a battery, and one or more of low-power and high-power circuitry. Low-power circuitry may be used for sensing cardiac signals including filtering, amplifying and digitizing sensed data. Low-power circuitry may also be used for certain cardiac therapy outputs such as pacing output, as well as an annunciator, such as a beeper or buzzer, telemetry circuitry for RF, conducted or inductive communication (or, alternatively, infrared, sonic and/or cellular) for use with a non-implanted programmer or communicator. The operational circuitry may also comprise memory and logic circuitry that will typically couple with one another via a control module which may include a controller or processor. High power circuitry such as high power capacitors, a charger, and an output circuit such as an H-bridge having high power switches may also be provided for delivering, for example, defibrillation therapy. Other circuitry and actuators may be included such as an accelerometer or thermistor to detected changes in patient position or temperature for various purposes, output actuators for delivering a therapeutic substance such as a drug, insulin or insulin replacement, for example.

Some illustrative examples for hardware, leads and the like for implantable defibrillators may be found in commercially available systems such as the Boston Scientific Teligen™ ICD and Emblem S-ICD™ System, Medtronic Concerto™ and Virtuoso™ systems, and St. Jude Medical Promote™ RF and Current™ RF systems, as well as the leads provided for use with such systems.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of implanting a lead for use in a cardiac stimulus system in a patient, the lead having a proximal end for coupling with an implantable pulse generator, a distal end, and at least one electrode thereon; the method comprising:
  inserting the lead into the venous system of the patient;
  advancing the distal end of the lead into the venous system and into the internal thoracic vein (ITV) of the patient; and
  advancing the distal end of the lead into an anterior intercostal vein from the ITV and to a desired location relative to the heart of the patient.

2. The method of claim 1 wherein the step of advancing the distal end of the lead into the venous system and into an ITV comprises advancing the distal end of the lead into the brachiocephalic vein and then into the ITV.

3. The method of claim 2 wherein the step advancing the distal end of the lead into the brachiocephalic vein comprises inserting an introducer sheath into one of the axillary, jugular, cephalic or subclavian veins of the patient and advancing the distal end of the lead through the introducer sheath.

4. The method of claim 1 further comprising advancing a guidewire into the ITV and using the guidewire to advance the distal end of the lead into the ITV.

5. The method of claim 1 wherein the step of advancing the distal end of the lead into the venous system and into the ITV comprises inserting the distal end of the lead into the superior epigastric vein and advancing the distal end of the lead superiorly into the ITV.

6. The method of claim 1 wherein the step of advancing the distal end of the lead into the venous system and into the ITV comprises inserting the distal end of the lead into the musculophrenic vein and advancing the distal end of the lead superiorly into the ITV.

7. The method of claim 1 wherein the step of advancing the distal end of the lead into the venous system and into the ITV comprises inserting the distal end of the lead through an intercostal space and into the ITV.

8. The method of claim 1, wherein:
  advancing the distal end of the lead into the intercostal vein from the ITV and to the desired location includes advancing the at least one electrode into the intercostal vein; and
  the method further comprises, after advancing the at least one electrode into the intercostal vein, delivering cardiac pacing therapy to the patient's heart using the at least one electrode in the anterior intercostal vein.

9. The method of claim 1, further comprising testing pacing thresholds using the at least one electrode.

10. A method of implanting a cardiac stimulus system comprising:
  implanting a first lead having a proximal end for coupling with an implantable pulse generator and a first electrode at a distal position on the first lead such that the first electrode resides in the internal thoracic vein (ITV) of a patient;
  implanting a second lead having a proximal end for coupling with the implantable pulse generator and a second electrode at a distal position on the lead such that the second electrode resides in a first subcutaneous position of the patient; and
  implanting the pulse generator at a second subcutaneous position of the patient, wherein the first and second subcutaneous positions are different.

11. The method of claim 10 wherein the step of implanting the pulse generator at a second subcutaneous location of the patient comprises implanting the pulse generator in a superior left pectoral position, wherein the first lead is implanted by first accessing one of the axillary, jugular, cephalic or subclavian veins of the patient and advancing the distal end of the lead therethrough into the left brachiocephalic vein and then into the left ITV.

12. The method of claim 10 wherein the step of implanting the pulse generator at a second subcutaneous location of the patient comprises implanting the pulse generator in an abdominal position, wherein the first lead is implanted by accessing either the superior epigastric vein or the musculophrenic vein and advancing the distal end of the first lead therethrough to the left ITV.

13. The method of claim 10 wherein the first subcutaneous location is in the left axilla.

14. A method of implanting a cardiac stimulus system comprising:
  accessing the internal thoracic vein of a patient at a first access location;
  advancing a first lead in a first direction in the internal thoracic vein from the first access location;
  advancing a second lead in a second direction in the internal thoracic vein from the first access location, wherein the first and second directions are different; and
  coupling the first and second leads to an implantable pulse generator.

15. The method of claim 14 wherein the first location is near the left axilla.

16. The method of claim 14 wherein the first lead comprises a first electrode, and the second lead comprises a second electrode, and the advancing steps are performed such that the first electrode is posterior of the heart, and the second electrode is anterior of the heart.

17. The method of claim 14 wherein the step of advancing the first lead in a first direction further comprises advancing a distal portion of the first lead into the internal thoracic vein of the patient.

18. The method of claim 14 wherein the step of advancing the second lead in a second direction further comprises advancing a distal portion of the second lead into one of the accessory hemiazygos, hemiazygos, or azygos veins.

19. The method of claim 14 further comprising implanting the implantable pulse generator at a subcutaneous location distant from the first access location, and placing the first and second leads in a tunnel between the subcutaneous location and the first access location.

20. The method of claim 10, further comprising delivering pacing therapy to the patient's heart using the first electrode and/or second electrode.

* * * * *